United States Patent
Liao et al.

(10) Patent No.: US 12,121,606 B2
(45) Date of Patent: *Oct. 22, 2024

(54) METHODS AND COMPOSITIONS FOR IMPROVING SKIN

(71) Applicant: L'OREAL, Paris (FR)

(72) Inventors: I-Chien Liao, Princeton, NJ (US); Patricia Brieva, Manalapan, NJ (US); Janet Wangari-Talbot, Ringoes, NJ (US); Charbel Bouez, Hoboken, NJ (US); Qian Zheng, Bridgewater, NJ (US); Kun Qian, Millburn, NJ (US)

(73) Assignee: L'OREAL, Paris (FR)

( * ) Notice: Subject to any disclaimer, the term of this patent is extended or adjusted under 35 U.S.C. 154(b) by 184 days.

This patent is subject to a terminal disclaimer.

(21) Appl. No.: 17/218,945

(22) Filed: Mar. 31, 2021

(65) Prior Publication Data

US 2022/0313579 A1 Oct. 6, 2022

(51) Int. Cl.
| | | |
|---|---|---|
| *A61K 8/42* | (2006.01) | |
| *A61K 8/06* | (2006.01) | |
| *A61K 8/34* | (2006.01) | |
| *A61K 8/368* | (2006.01) | |
| *A61K 8/37* | (2006.01) | |
| *A61K 8/49* | (2006.01) | |
| *A61K 8/73* | (2006.01) | |
| *A61K 8/891* | (2006.01) | |
| *A61K 8/92* | (2006.01) | |
| *A61K 8/9789* | (2017.01) | |
| *A61Q 19/00* | (2006.01) | |

(52) U.S. Cl.
CPC .............. *A61K 8/42* (2013.01); *A61K 8/06* (2013.01); *A61K 8/345* (2013.01); *A61K 8/368* (2013.01); *A61K 8/37* (2013.01); *A61K 8/4913* (2013.01); *A61K 8/735* (2013.01); *A61K 8/891* (2013.01); *A61K 8/922* (2013.01); *A61K 8/927* (2013.01); *A61K 8/9789* (2017.08); *A61Q 19/00* (2013.01); *A61K 2800/48* (2013.01)

(58) Field of Classification Search
None
See application file for complete search history.

(56) References Cited

U.S. PATENT DOCUMENTS

| | | |
|---|---|---|
| 6,945,952 B2 | 9/2005 | Kwon |
| 10,449,133 B1 | 10/2019 | Faig et al. |
| 2005/0065463 A1 | 3/2005 | Tobinaga et al. |
| 2007/0202203 A1 | 8/2007 | Amar |
| 2011/0021438 A1 | 1/2011 | Dalko et al. |
| 2015/0250707 A1 | 9/2015 | Lee |
| 2015/0335560 A1 | 11/2015 | Bernard et al. |
| 2016/0206546 A1 | 7/2016 | Fernandes et al. |
| 2017/0172903 A1 | 6/2017 | El Akkari et al. |
| 2017/0224760 A1* | 8/2017 | Garruto ............... A61K 8/97 |
| 2017/0348221 A1 | 12/2017 | Maruyama et al. |
| 2018/0280270 A1 | 10/2018 | Rughani et al. |
| 2020/0276099 A1 | 9/2020 | Robbins et al. |

FOREIGN PATENT DOCUMENTS

| | | | |
|---|---|---|---|
| EP | 1897526 A1 | 3/2008 | |
| FR | 2878155 A1 | 5/2006 | |
| FR | 2897776 A1 | 3/2007 | |
| FR | 2895256 A1 | 6/2007 | |
| FR | 2905069 A1 * | 2/2008 | .............. A61K 8/06 |
| FR | 3090381 A1 | 6/2020 | |
| WO | 2004000389 A2 | 12/2003 | |
| WO | 2008053198 A1 | 5/2008 | |
| WO | 2012131623 A2 | 10/2012 | |
| WO | 2013088368 A2 | 6/2013 | |
| WO | 2014180808 A1 | 11/2014 | |

OTHER PUBLICATIONS

Richter et al., Clinics Review Articles, Multicultural Aesthetics in Facial Plastic Surgery, Editor: J. Regan Thomas, Aug. 2014, vol. 22, No. 3 (Year: 2014).*
PE2E machine translation of FR-2905069-A1, Feb. 2008 (Year: 2008).*
Database GNPD [Online] Mintel; Anonymous: "Eye Cream," 2021 XP055902004.
Preliminary Search Report and Written Opinion issued on Mar. 23, 2022 for corresponding French Application No. FR2107473.

* cited by examiner

*Primary Examiner* — Jennifer A Berrios
(74) *Attorney, Agent, or Firm* — POLSINELLI PC

(57) ABSTRACT

A method for improving skin comprising reducing the barrier function of skin, and applying a skin treatment composition to the skin. The skin treatment composition may include about 0.1 to about 25 wt. % of acetyl trifluoromethylphenyl valylglycine; about 0.5 to about 30 wt. % of a polyol; about 0.1 to about 30 wt. % of a silicone, fatty compound, or a mixtures thereof, wherein the skin treatment composition is an emulsion, and all weight percentages are based on the total weight of the skin treatment composition.

20 Claims, 15 Drawing Sheets

METHODS AND COMPOSITIONS FOR IMPROVING SKIN

FIELD OF THE DISCLOSURE

The instant disclosure relates to methods for improving skin using a unique combination of a skin treatment process in conjunction with certain skin treatment compositions.

BACKGROUND OF THE DISCLOSURE

Fractional skin treatments are typically used to damage certain layers of the skin in order to facilitate the growth of skin cells. Several types of fractional treatments exist. It is a known practice to use microneedles arranged in the form of a network, which perforate the upper layers of the skin to create microholes. For example, U.S. patent application no. 2008/0268007, which is incorporated herein in its entirety for all purposes, discloses a patch comprising such a biodegradable matrix of microprobes.

Another known technique is based on the use of a laser and an optical system which, for example, separates the ray emitted by a laser into a multitude of relatively fine rays that constitute a plurality of treatment points at the points of impact with the skin, said skin undergoing at each point of impact a photothermolysis that excavates a microwell.

Although a fractional treatment is less aggressive than a treatment on a continuous area of skin, certain devices may nevertheless cause discomfort during their application. There is consequently a need for improved methods for improving skin using a skin treatment procedure.

SUMMARY OF THE DISCLOSURE

The instant disclosure relates to methods for improving skin using a unique combination of a skin treatment process in conjunction with certain skin treatment compositions. The inventors surprisingly discovered that superior anti-aging benefits for the skin, such as skin elasticity, skin texture, smoothness, skin volume, wrinkle reduction, and the like, are obtained using the unique combination of the skin treatment processes and skin treatment compositions disclosed herein. In many instances, the combination of particular skin treatment processes in conjunction with certain skin treatment compositions yielded synergistic results, which unexpectedly improved skin.

For example, the inventors were surprised by the clinically measureable benefits to crow's feet wrinkle, under eye wrinkles, skin radiance, skin tone and skin roughness provided by exemplary methods of the instant disclosure—particularly in comparison to comparative methods using commercial benchmark products. Not only did certain exemplary methods provide enhanced anti-ageing properties, certain exemplary methods provided faster kinetics of achieving clinically relevant levels of change, which was surprising in view of experiments using a comparative method with benchmark compositions.

The methods for improving skin, according to an aspect of the disclosure, typically comprise:
(a) reducing the barrier function of skin; and
(b) applying a skin treatment composition to the skin, the skin treatment composition comprising:
  (i) about 0.1 to about 25 wt. % of acetyl trifluoromethylphenyl valylglycine; and
  (ii) about 0.1 to about 30 wt. % of a silicone, fatty compound, or a combination thereof, wherein the skin treatment composition is an emulsion, and all weight percentages are based on the total weight of the skin treatment composition.

The barrier function of the skin may be reduced by applying, to the skin, a laser (e.g., fractional or non-fractional, and/or ablative or non-ablative) procedure, a microneedle procedure, a cryotherapy procedure, a radiofrequency microneedle procedure, or a combination thereof. In some instances, the barrier function of the skin is reduced by applying a fractional laser procedure. In other instances, the barrier function of the skin is reduced by applying a fractional microneedle procedure, a fractional radiofrequency microneedle procedure, or a combination thereof. In at least one embodiment, the fractional procedure includes applying a fractional laser to the skin, the fractional laser having an energy range of about 4 to 160 $kJ/cm^2$ and an irradiance of about 25 $kW/cm^2$ to about 4 $MW/cm^2$.

The skin treatment composition may be applied to the skin before the application of the fractional microneedle procedure, the fractional radiofrequency microneedle procedure, or the combination thereof. Additionally or alternatively, the skin treatment composition may be applied to the skin after the application of the fractional microneedle procedure, the fractional radiofrequency microneedle procedure, or the combination thereof. Preferably, the skin treatment composition is applied to the skin within 24 hours of the reduction of the barrier function. The skin treatment composition may be applied at least twice over a period of a month. For some embodiments, the skin treatment composition is formulated for application to skin at least once a day or, e.g., at least twice a day.

The skin treatment composition may be applied in an amount such that about 0.1 gram or more of acetyl trifluoromethylphenyl valylglycine is applied to the skin. The skin treatment composition may comprise about 1 to about 30 wt. % of a fatty compound chosen from a fatty alcohol, a fatty ester, a fatty ether, a fatty acid, a hydrocarbon oil, derivatives thereof, or mixtures thereof. In some embodiments, the skin treatment composition comprises a fatty alcohol chosen decyl alcohol, undecyl alcohol, dodecyl alcohol, myristyl alcohol, lauryl alcohol, cetyl alcohol, stearyl alcohol, cetearyl alcohol, isostearyl alcohol, isocetyl alcohol, behenyl alcohol, linalool, oleyl alcohol, cis-4-t-butylcyclohexanol, isotridecyl alcohol, myricyl alcohol, arachidyl alcohol, and mixtures thereof.

Additionally or alternatively, the skin treatment composition may comprises a hydrocarbon oil that is a plant based hydrocarbon oil chosen from coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, castor oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, or mixtures thereof. The skin treatment composition may include about 1 to about 30 wt. % of a silicone chosen from lauryl peg-9 polydimethylsiloxyethyl dimethicone, dimethylsiloxane, polydimethylsiloxane, polydimethylsiloxane, dimethicone, acrylate/dimethicone polymer, and mixtures thereof. In some embodiments, the skin treatment composition is formulated to have a polyol chosen from ethylene glycol, propylene glycol, butylene glycol, hexylene glycol, pentylene glycol, diethylene glycol, dipropylene glycol, 1,3 propanediol, glycerin, polyethylene glycols, and a mixture thereof.

The skin treatment composition may be formulated to be a cream, a lotion, a serum, or an ampoule. The skin treatment composition may have a viscosity of about 1 to about 10,000 cPs or, e.g., about 1,000 to about 10,000 cPs, at a temperature of 24° C. as measured with RV-4 Disk spindle on a Brookfield DV2T viscometer at a range of 5-20 rpm after 90 seconds. Preferably, the method yields a proliferation of senescent cells that is 10% or greater than the proliferation of senescent cells that receive the same skin treatment procedure without a skin treatment composition.

BRIEF DESCRIPTION OF THE FIGURES

Implementation of the present technology will now be described, by way of example only, with reference to the attached figures, wherein.

Figure 1:
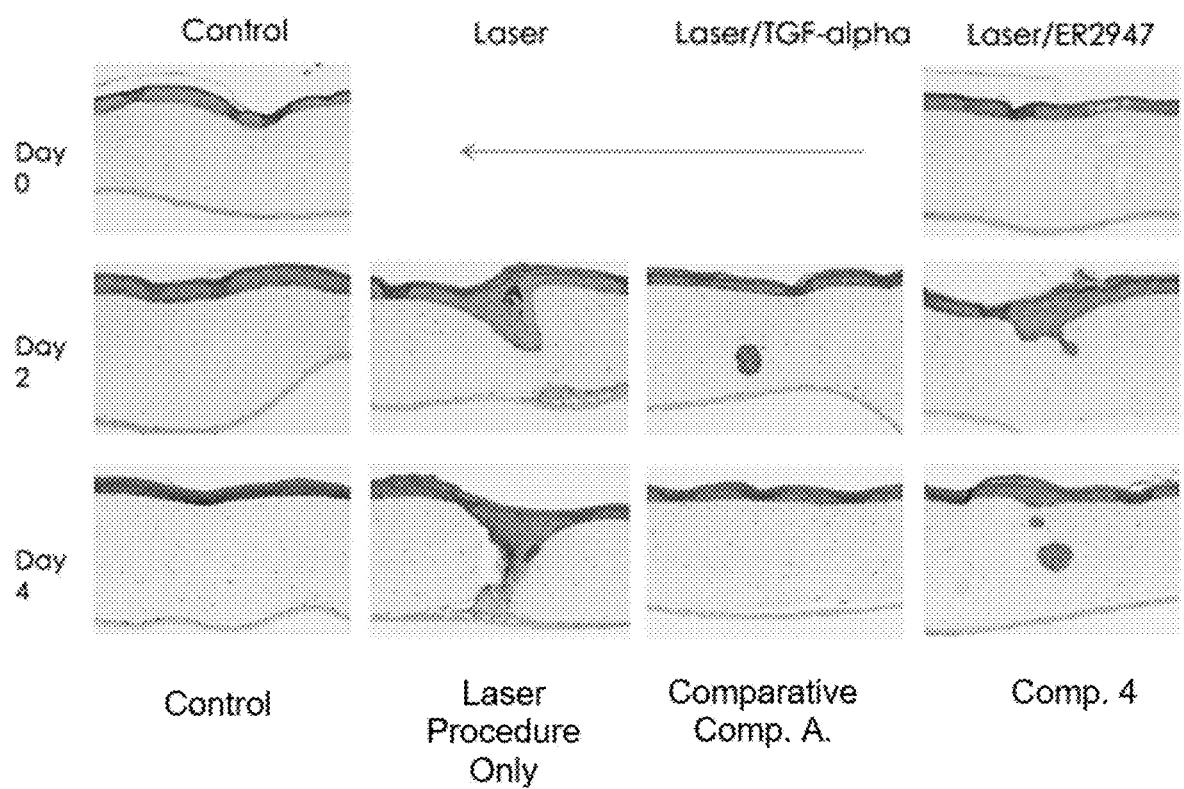
FIG. 1 is images of in vitro skin samples at 0 day, 2 days, and 4 days after the fractional laser procedure and the application of either a comparative composition or a non-limiting exemplary skin treatment composition according to aspects of the disclosure.

It should be understood that the various aspects are not limited to the arrangements and instrumentality shown in the drawings.

DETAILED DESCRIPTION OF THE DISCLOSURE

The instant disclosure relates to methods for improving skin using a unique combination of a skin treatment process in conjunction with certain skin treatment compositions. The inventors surprisingly discovered that enhanced anti-aging benefits for the skin, such as skin elasticity, skin texture, smoothness, skin volume, wrinkle reduction, and the like, may be obtained using the unique combination of the skin treatment processes and skin treatment compositions. In many instances, the combination of particular skin treatment processes in conjunction with certain skin treatment compositions yielded synergistic results, which unexpectedly improved skin.

The methods for improving skin, according to an aspect of the disclosure, typically comprise:
  (a) reducing the barrier function of skin; and
  (b) applying a skin treatment composition to the skin, the skin treatment composition comprising:
    (i) about 0.1 to about 25 wt. % of acetyl trifluoromethylphenyl valylglycine; and
    (ii) about 0.1 to about 30 wt. % of a silicone, fatty compound, or a combination thereof,
      wherein the skin treatment composition is an emulsion, and all weight percentages are based on the total weight of the skin treatment composition.

Typically, the methods disclosed herein utilize skin treatment procedures chosen from laser procedures, microneedle procedures, cryotherapy procedures, radiofrequency microneedle procedures, or combinations thereof to reduce the barrier function of the skin. In some embodiments, the methods disclosed herein utilize a laser procedure for reducing the barrier function of the skin. The laser procedure may be ablative or non-ablative and, in some cases, may be fractional or non-fractional laser procedures. For example, the laser procedure may use a fractional laser that is non-ablative.

A fractional laser affects the surface of the stratum corneum to create, by local photothermo lysis, a plurality of spaced-apart pores (microwells) in the upper layers of the skin. Preferably, to fractionate the impacts of the laser and space them out over the skin, preferably evenly spaced, the laser system may comprise a motorized scanner that comprises one or more rotary mirrors whose rotation speed causes scanning of the laser spot. Depending on the fractional laser used, the scanning may take place along different paths: circular, rectangular or square scanning, or random scanning. The fractional laser treatment may comprise several successive passes of the laser over a given area so as to obtain better homogeneity of the treatment. On each pass, new points of impact are created, spaced from the previous points of impact. An example of a non-ablative fractional laser is the machine sold by the company Solta under the brand name Fraxel re:store® Dual (1927 nm). Additional examples of fractional lasers are described in U.S. patent application no. 2008/0208179, which is incorporated herein in its entirety for all purposes.

The wavelength of the fractional laser may be in the inferred (IR) range. For example, the laser procedure may use a fractional laser having a wavelength of about 1100 nm to about 2500 nm, preferably about 1400 to about 200, or preferably about 1430 to about 1950. The treatment depth may be from about 200 µm to about 1.4 mm. In some instances, the treatment depth is from about 550 µm to about 1.4 mm, about 800 µm to about 1.4 mm, or about 1120 µm to about 1.4 mm.

A greater treatment depth and wider wells are obtained when the light power is stronger. The size of a microwell may range, for example, from about 0.5 µm in diameter to about 500 µm in diameter, or from about 50 µm to about 350 µm. The density of the microwells (also known as pores) created by the laser procedure may be from about 100 to about 10,000 microwells per square centimeter ($cm^2$). In some cases, the density of the microwells per square centimeter is from about 100 to about 9,000, about 100 to about 8,000, about 100 to about 7,000, about 100 to about 6,000, about 100 to about 5,000, about 100 to about 4,000, about 100 to about 3,000, about 100 to about 2,000, or about 100 to about 1,000.

The irradiance, which measures the power density received by the skin to be treated, is preferably from about 25 kW/$cm^2$ to about 4 MW/$cm^2$. The fluence of the laser treatment, which measures the energy density received on the area of skin to be treated, is preferably from about 4 kJ/$cm^2$ to about 160 kJ/$cm^2$. The energy of a laser pulse to create a microwell may range from about 0.1 mJ to about 50 mJ.

Additional description of laser procedures for reducing the skin barrier function while at the same time preserving the skin's capacity for protecting the body against infection may be found in U.S. patent publication no. 2008/0208179 and PCT publication no. WO 2008/053198, which are incorporated herein in their entirety for all purposes.

The methods may, additionally or alternatively, utilize a microneedle procedure to reduce the barrier function of the skin. The microneedles may be solid (e.g., hollow needles or not hollow needles), for the purpose of microperforation, or soluble, enabling the ends to break off after perforation and formation of microimplants with gradual dissolution over time. The microneedles may, thus, comprise an orifice for administering a skin treatment composition as described herein, or may be devoid of an orifice. In some instances, the microneedles may be used as skin microperforators, facilitating the subsequent application of one or more active agents. Examples of microneedles and microneedle procedures are described in PCT patent publication no. WO 2007/061964; PCT patent publication no. WO 2004/000389; U.S. Pat. No. 6,945,952; PCT patent publication no. WO 2004/024224; Japanese patent publication no. 2005/154321; PCT patent publication no. 2007/023167; U.S. patent publication no. 2005/065463; PCT patent publication no. WO 03/092785; Japanese patent publication no. 2005/154321; PCT patent publication no. WO 2007/023167; U.S. patent publication no. 2005/065463; and PCT patent publication no. WO 03/092785, which are all incorporated herein for all purposes in their entirety.

In some cases, the methods disclosed herein may use a radiofrequency microneedle procedure to reduce the barrier function of the skin. Radiofrequency microneedle procedures may utilize one or more electrodes, such as monopolar RF electrodes, imparting perforations into one or more tissue layers of the skin. The electrodes are typically provided in a pattern to impart a corresponding pattern of perforations in one or more tissue layers. Further description of radiofrequency microneedle devices and procedures thereof are described in European patent no. 1742590; U.S. Pat. Nos. 8,317,782; and 6,277,116, which are all incorporated herein for all purposes in their entirety.

Additionally or alternatively, the methods disclosed herein may use a cryotherapy microneedle procedure to reduce the barrier function of the skin. The cryotherapy microneedle procedures may either cool or heat the skin to damage and reduce the skin barrier function. For instance, the cryotherapy microneedle procedure may apply electromagnetic waves in a pulsed mode or in a continuous mode to reduce the skin barrier function. Additional description of cryotherapy microneedle procedures and devices thereof may be found in U.S. Pat. Nos. 8,548,599 and 7,367,341, which are both incorporated herein for all purposes in their entirety.

The methods for improving skin typically include applying a skin treatment composition to the skin within 24 hours of the skin treatment procedure. In some cases, it is preferable that the skin treatment composition is applied within about 20 hours, within about 16 hours, within about 12 hours, within about 10 hours, within about 8 hours, within about 6 hours, within about 4 hours, within about 2 hours, within about 1 hour after the application of the skin treatment procedure. Additionally or alternatively, the skin treatment composition may be applied before the application of the skin treatment procedure to the skin. For example, the skin treatment composition may applied within 24 hours, within about 20 hours, within about 16 hours, within about 12 hours, within about 10 hours, within about 8 hours, within about 6 hours, within about 4 hours, within about 2 hours, within about 1 hour before the application of the skin treatment procedure.

The methods may preferably include applying the skin treatment composition to the skin more than one time before or after the application of the skin treatment procedure. In some cases, the skin treatment composition is applied at least twice over a period of a month. In further cases, the skin treatment composition is applied at least three times, at least four times, at least five times, at least six times, at least seven times, at least eight times, at least nine times, or at least ten times over a period of time (e.g., one week, two weeks, three weeks, a month, two months, three months, etc.). The method may include applying the skin treatment a plurality of times (e.g., one, two, three, four, five, or six times) each day for a period of time (e.g., one week, two weeks, three weeks, a month, two months, three months, etc.).

Additionally or alternatively, the methods for improving skin may include applying an amount of the skin treatment composition such that about 0.1 gram or more of acetyl trifluoromethylphenyl valylglycine is applied to the skin. For example, the skin treatment composition may be applied such that about 0.1 gram per decimeter (g/$dm^2$) or more, about 0.5 g/$dm^2$ or more, about 07.5 g/$dm^2$ or more, about 1 g/$dm^2$ or more, about 1.5 g/$dm^2$ or more, about 2 g/$dm^2$ or more, about 2.5 g/$dm^2$ or more, or about 3 g/$dm^2$ or more of acetyl trifluoromethylphenyl valylglycine is applied to the skin. In some cases, the, the skin treatment composition is applied such that about 0.1 to about 10 gram per decimeter (g/dm$^2$), about 0.1 to about 9 g/dm$^2$, about 0.1 to about 8 g/dm$^2$, about 0.1 to about 7 g/dm$^2$, about 0.1 to about 6 g/dm$^2$, about 0.1 to about 5 g/dm$^2$, about 0.1 to about 4 g/dm$^2$, about 0.1 to about 3 g/dm$^2$, about 0.1 to about 2 g/dm$^2$, about 0.1 to about 1 g/dm$^2$; about 0.5 to about 10 gram per decimeter (g/dm$^2$), about 0.5 to about 9 g/dm$^2$, about 0.5 to about 8 g/dm$^2$, about 0.5 to about 7 g/dm$^2$, about 0.5 to about 6 g/dm$^2$, about 0.5 to about 5 g/dm$^2$, about 0.5 to about 4 g/dm$^2$, about 0.5 to about 3 g/dm$^2$, about 0.5 to about 2 g/dm$^2$, about 0.5 to about 1 g/dm$^2$; or about 1 to about 10 gram per decimeter (g/dm$^2$), about 1 to about 9 g/dm$^2$, about 1 to about 8 g/dm$^2$, about 1 to about 7 g/dm$^2$, about 1 to about 6 g/dm$^2$, about 1 to about 5 g/dm$^2$, about 1 to about 4 g/dm$^2$, about 1 to about 3 g/dm$^2$, or about 1 to about 2 g/dm$^2$ of acetyl trifluoromethylphenyl valylglycine is applied to the skin.

According to another aspect of the disclosure, provided is a use of the skin treatment compositions disclosed herein for improving skin, e.g., after a fractional procedure or an ablative procedure. In one embodiment, provided is a use of a skin treatment composition for improving skin comprising:
(a) reducing the barrier function of skin; and
(b) applying a skin treatment composition to the skin, the skin treatment composition comprising:
(i) about 0.1 to about 25 wt. % of acetyl trifluoromethylphenyl valylglycine; and
(ii) about 0.1 to about 30 wt. % of a silicone, fatty compound, or a combination thereof,
wherein the skin treatment composition is an emulsion, and all weight percentages are based on the total weight of the skin treatment composition.

The skin treatment compositions may include various ingredient and/or components, but typically comprise:
(i) about 0.1 to about 25 wt. % of acetyl trifluoromethylphenyl valylglycine; and
(ii) about 0.1 to about 30 wt. % of a silicone, fatty compound, or a combination thereof,
wherein all weight percentages are based on the total weight of the skin treatment composition.

The skin treatment compositions are preferably formulated to be a cream, a lotion, a serum, or an ampoule. For example, the skin treatment compositions may have water-in-oil emulsions, oil-in-water emulsions, silicone-in-water emulsions, water-in-silicone emulsions, or combinations thereof.

In some embodiments, it may be desirable for the skin treatment composition to not be a gel (e.g., comprising or in a gel layer on a substrate). Thus, in some cases, the total amount of gelling agents/ingredients, such as water-swellable polymers and/or water-insoluble polymers, is less than about 10 wt. %, less than about 9 wt. %, less than about 8 wt. %, less than about 7 wt. %, less than about 6 wt. %, less than about 5 wt. %, less than about 4 wt. %, less than about 3 wt. %, less than about 2 wt. %, less than about 1 wt. %, or less than about 0.5 wt. %, based on the total weight of the skin treatment compositions.

Additionally or alternatively, the skin treatment compositions may be transparent. The term "transparent" with respect to a transparent composition indicates that the composition has transmittance of at least 80% at a wavelength of 600 nm, for example measured using a Lambda 40 UV-visible spectrometer. The skin treatment compositions may have, for example, a transmittance of at least 80%, at least 90%, or at least 95% at a wavelength of 600 nm, measured, for example, using a Lambda 40 UV-visible spectrometer.

The term "clear" is interchangeable with the term "transparent" for purposes of the instant disclosure.

The skin treatment compositions may be formulated to have a viscosity of about 1 to about 10,000 cPs at a temperature of 24° C. as measured with RV-4 Disk spindle on a Brookfield DV2T viscometer at a range of 5-20 rpm after 90 seconds. For example, the skin treatment composition may have a viscosity of about 1 to about 10,000 cPs, about 1 to about 9,000 cPs, about 1 to about 8,000 cPs, about 1 to about 7,000 cPs, about 1 to about 6,000 cPs, about 1 to about 5,000 cPs, about 1 to about 4,000 cPs, about 1 to about 3,000 cPs, about 1 to about 2,000 cPs, about 1 to about 1,000 cPs, about 1 to about 500 cPs, about 1 to about 250 cPs, about 1 to about 100 cPs; about 100 to about 10,000 cPs, about 100 to about 9,000 cPs, about 100 to about 8,000 cPs, about 100 to about 7,000 cPs, about 100 to about 6,000 cPs, about 100 to about 5,000 cPs, about 100 to about 4,000 cPs, about 100 to about 3,000 cPs, about 100 to about 2,000 cPs, about 100 to about 1,000 cPs, about 100 to about 500 cPs, about 100 to about 250 cPs; about 500 to about 10,000 cPs, about 500 to about 9,000 cPs, about 500 to about 8,000 cPs, about 500 to about 7,000 cPs, about 500 to about 6,000 cPs, about 500 to about 5,000 cPs, about 500 to about 4,000 cPs, about 500 to about 3,000 cPs, about 500 to about 2,000 cPs, about 500 to about 1,000 cPs; about 1,000 to about 10,000 cPs, about 1,000 to about 9,000 cPs, about 1,000 to about 8,000 cPs, about 1,000 to about 7,000 cPs, about 1,000 to about 6,000 cPs, about 1,000 to about 5,000 cPs, about 1,000 to about 4,000 cPs, about 1,000 to about 3,000 cPs, about 1,000 to about 2,000 cPs; about 3,000 to about 10,000 cPs, about 3,000 to about 9,000 cPs, about 3,000 to about 8,000 cPs, about 3,000 to about 7,000 cPs, about 3,000 to about 6,000 cPs, about 3,000 to about 5,000 cPs; about 5,000 to about 10,000 cPs, about 5,000 to about 9,000 cPs, about 5,000 to about 8,000 cPs, about 5,000 to about 7,000 cPs; about 7,000 to about 10,000 cPs, about 7,000 to about 9,000 cPs, at a temperature of 24° C. as measured with RV-4 Disk spindle on a Brookfield DV2T viscometer at a range of 5-20 rpm after 90 seconds.

Suitable components, such as those listed below, may be included or excluded from the formulations for the skin treatment compositions depending on the specific combination of other components, the form of the skin treatment composition (e.g., a cream, a lotion, a serum, or an ampoule), and/or the use of the skin treatment composition.

Acetyl Trifluoromethylphenyl Valylglycine

The skin tightening compositions include an amount of acetyl trifluoromethylphenyl valylglycine that may vary, but typically is from about 0.1 to about 25 wt. %, based on the total weight of the skin treatment composition. For example, the amount of acetyl trifluoromethylphenyl valylglycine present in the skin treatment composition may be from about 0.1 to about 25 wt. %, about 0.1 to about 22 wt. %, about 0.1 to about 19 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 25 wt. %, about 0.25 to about 22 wt. %, about 0.25 to about 19 wt. %, about 0.25 to about 16 wt. %, about 0.25 to about 14 wt. %, about 0.25 to about 12 wt. %, about 0.25 to about 10 wt. %, about 0.25 to about 8 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 25 wt. %, about 0.5 to about 22 wt. %, about 0.5 to about 19 wt. %, about 0.5 to about 16 wt. %, about 0.5 to about 14 wt. %, about 0.5 to about 12 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 25 wt. %, about 0.75 to about 22 wt. %, about 0.75 to about 19 wt. %, about 0.75 to about 16 wt. %, about 0.75 to about 14 wt. %, about 0.75 to about 12 wt. %, about 0.75 to about 10 wt. %, about 0.75 to about 8 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 25 wt. %, about 1 to about 22 wt. %, about 1 to about 19 wt. %, about 1 to about 16 wt. %, about 1 to about 14 wt. %, about 1 to about 12 wt. %, about 1 to about 10 wt. %, about 1 to about 8 wt. %, about 1 to about 6 wt. %, about 1 to about 5 wt. %, about 1 to about 4 wt. %, about 1 to about 3 wt. %, about 1 to about 2 wt. %; about 2 to about 25 wt. %, about 2 to about 22 wt. %, about 2 to about 19 wt. %, about 2 to about 16 wt. %, about 2 to about 14 wt. %, about 2 to about 12 wt. %, about 2 to about 10 wt. %, about 2 to about 8 wt. %, about 2 to about 6 wt. %, about 2 to about 5 wt. %, about 2 to about 4 wt. %, about 2 to about 3 wt. %; about 5 to about 25 wt. %, about 5 to about 22 wt. %, about 5 to about 19 wt. %, about 5 to about 16 wt. %, about 5 to about 14 wt. %, about 5 to about 12 wt. %, about 5 to about 10 wt. %, about 5 to about 8 wt. %; about 7.5 to about 27.5 wt. %, about 7.5 to about 22 wt. %, about 7.5 to about 19 wt. %, about 7.5 to about 16 wt. %, about 7.5 to about 14 wt. %, about 7.5 to about 12 wt. %, about 7.5 to about 10 wt. %; about 10 to about 27.5 wt. %, about 10 to about 22 wt. %, about 10 to about 19 wt. %, about 10 to about 16 wt. %, about 10 to about 14 wt. %, about 10 to about 12 wt. %; about 15 to about 27.5 wt. %, about 15 to about 22 wt. %, about 15 to about 19 wt. %; about 20 to about 27.5 wt. %, about 20 to about 22 wt. %, including ranges and subranges therebetween, based on the total weight of the skin treatment composition.

Polyol(s)

The skin treatment composition may, preferably, include one or more polyols. The total amount of polyols in the skin treatment composition may vary from, e.g., about 0.5 to about 30 wt. %, based on the total weight of the skin treatment composition. For example, the total amount of polyols may be from about 0.5 to about 30 wt. %, about 0.5 to about 25 wt. %, about 0.5 to 20 wt. %, about 0.5 to about 18 wt. %, about 0.5 to about 16 wt. %, about 0.5 to about 14 wt. %, about 0.5 to about 12 wt. %, about 0.5 to about 10 wt. %, about 0.5 to about 8 wt. %, about 0.5 to about 7 wt. %, about 0.5 to about 6 wt. %, about 0.5 to about 5 wt. %; about 1 to about 30 wt. %, about 1 to about 25 wt. %, about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 2 to about 30 wt. %, about 2 to about 25 wt. %, about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 2 to about 7 wt. %, about 2 to about 6 wt. %, about 2 to about 5 wt. %; about 3 to about 30 wt. %, about 3 to about 25 wt. %, about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 8 wt. %, about 3 to about 7 wt. %, about 3 to about 6 wt. %, about 3 to about 5 wt. %; about 4 to about 30 wt. %, about 4 to about 25 wt. %, about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. % about 4 to about 7 wt. %, about 4 to about 6 wt. %, about 4 to about 5 wt. %; about 5 to about 30 wt. %, about 5 to about 25 wt. %, about 5 to about 20 wt. %, about 5 to about 18 wt. %, about 5 to about 16 wt. %, about 5 to about 14 wt. %, about 5 to about 12 wt. %, about 5 to about 10 wt. %, about 5 to about 8 wt. %, about 5 to about 7 wt. %, about 5 to about 6 wt. %; about 7 to about 30 wt. %, about 7 to about 25 wt. %, about 7 to about 20 wt. %, about 7 to about 18 wt. %, about 7 to about 16 wt. %, about 7 to about 14 wt. %, about 7 to about 12 wt. %, about 7 to about 10 wt. %; about 10 to about 30 wt. %, about 10 to about 25 wt. %, about 10 to about 20 wt. %, about 10 to about 18 wt. %, about 10 to about 16 wt. %, about 10 to about 14 wt. %, about 10 to about 12 wt. %; about 12.5 to about 30 wt. %, about 12.5 to about 25 wt. %, about 12.5 to about 20 wt. %, about 12.5 to about 18 wt. %, about 12.5 to about 16 wt. %; about 15 to about 30 wt. %, about 15 to about 25 wt. %, about 15 to about 20 wt. %, about 15 to about 18 wt. %, or about 15 to about 16 wt. %, including all ranges and sub-ranges therebetween, based on the total weight of the skin treatment composition.

The polyols of the skin treatment composition may comprise or be chosen from polyols having from 2 to 15 carbon atoms and at least two hydroxyl groups. Exemplary polyols that may be used in the skin treatment composition include and/or may be chosen from alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; sorbitol; sorbitan; triacetin; and a mixture thereof.

The polyol(s) may be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol. In one instance, the one or more polyols include or are chosen from ethylene glycol, propylene glycol, butylene glycol, hexylene glycol, pentylene glycol, 1,3-propanediol, diethylene glycol, dipropylene glycol, caprylyl glycol, glycerin, and a mixture thereof. In another instance, the skin treatment composition includes or is chosen from caprylyl glycol, glycerin, and a mixture thereof.

Silicone(s), Fatty Compound(s), or Mixtures Thereof

The skin treatment compositions include one or more silicone(s), fatty compound(s), or mixtures thereof in amount that my vary, but is typically about 0.1 to about 30 wt. %, based on the total weight of the skin treatment compositions. In some instances, the amount of silicone(s), fatty compound(s), or mixtures thereof present in the skin treatment compositions is about 0.1 to about 30 wt. %, about 0.1 to about 25 wt. %, about 0.1 to 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 7 wt. %, about 0.1 to about 6 wt. %, about 0.1 to about 5 wt. %; about 0.5 to about 30 wt. %, about 0.5 to about 25 wt. %, about 0.5 to 20 wt. %, about 0.5 to about 18 wt. %, about 0.5 to about 16 wt. %, about 0.5 to about 14 wt. %, about 0.5 to about 12 wt. %, about 0.5 to about 10 wt. %, about 0.5 to about 8 wt. %, about 0.5 to about 7 wt. %, about 0.5 to about 6 wt. %, about 0.5 to about 5 wt. %; about 1 to about 30 wt. %, about 1 to about 25 wt. %, about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 2 to about 30 wt. %, about 2 to about 25 wt. %, about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 2 to about 7 wt. %, about 2 to about 6 wt. %, about 2 to about 5 wt. %; about 3 to about 30 wt. %, about 3 to about 25 wt. %, about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 8 wt. %, about 3 to about 7 wt. %, about 3 to about 6 wt. %, about 3 to about 5 wt. %; about 4 to about 30 wt. %, about 4 to about 25 wt. %, about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. % about 4 to about 7 wt. %, about 4 to about 6 wt. %, about 4 to about 5 wt. %; about 5 to about 30 wt. %, about 5 to about 25 wt. %, about 5 to about 20 wt. %, about 5 to about 18 wt. %, about 5 to about 16 wt. %, about 5 to about 14 wt. %, about 5 to about 12 wt. %, about 5 to about 10 wt. %, about 5 to about 8 wt. %, about 5 to about 7 wt. %, about 5 to about 6 wt. %; about 7.5 to about 30 wt. %, about 7.5 to about 25 wt. %, about 7.5 to about 20 wt. %, about 7.5 to about 18 wt. %, about 7.5 to about 16 wt. %, about 7.5 to about 14 wt. %, about 7.5 to about 12 wt. %, about 7.5 to about 10 wt. %; about 10 to about 30 wt. %, about 10 to about 25 wt. %, about 10 to about 20 wt. %, about 10 to about 18 wt. %, about 10 to about 16 wt. %, about 10 to about 14 wt. %, about 10 to about 12 wt. %; about 12.5 to about 30 wt. %, about 12.5 to about 25 wt. %, about 12.5 to about 20 wt. %, about 12.5 to about 18 wt. %, about 12.5 to about 16 wt. %; about 15 to about 30 wt. %, about 15 to about 25 wt. %, about 15 to about 20 wt. %, about 15 to about 18 wt. %, or about 15 to about 16 wt. %, including all ranges and sub-ranges therebetween, based on the total weight of the skin treatment composition.

Silicone(s)

The skin treatment compositions may include one or more silicones. The silicones may, optionally, be functionalized with an amino group or functionalized with a methacrylic group. The term "amino-functionalized silicone" or "amino silicones" means a silicone containing at least one primary amino, secondary amino, tertiary amino and/or quaternary ammonium group. The structure of the amino-functionalized silicone may be linear or branched, cyclic or non-cyclic. The amino functional group may be at any position in the silicone molecule, preferably at the end of the backbone (for example, in the case of amodimethicones) and/or in the side chain.

Non-limiting examples of silicones include amine-functionalized silicones (e.g., amodimethicone), dimethicone, bis-aminopropyl dimethicone, trimethyl silylamodimethicone, dimethicone copolyols, etc. The skin treatment composition may include, in some instances, one or more silicones chosen from polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), bis-aminopropyl dimethicone, trimethylsilylamodimethicone, dimethicone copolyols, dimethicone copolyol esters, dimethicone copolyol quaternium nitrogen containing compounds, dimethicone copolyol phosphate esters, and mixtures thereof. For example, the one or more silicones may be or include one or more dimethicone copolyols. The copolyols may be chosen from Dimethicone PEG-8 Adipate, Dimethicone PEG-8 Benzoate, Dimethicone PEG-7 Phosphate, Dimethicone PEG-10 Phosphate, Dimethicone PEG/PPG-20/23 Benzoate, Dimethicone PEG/PPG-7/4 Phosphate, Dimethicone PEG/PPG-12/4 Phosphate, PEG-3 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-6/11 Dimethicone, PEG/PPG-8/14 Dimethicone, PEG/PPG-14/4 Dimethicone, PEG/PPG-15/15 Dimethicone, PEG/PPG-16/2 Dimethicone, PEG/PPG-17/18 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, and a mixture thereof.

The silicone(s) may, optionally, include or be chosen from a siloxane with a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

One or more silicone(s) may be included in the skin treatment composition has an emulsifier. For example, the silicone may be an organosiloxane emulsifier, oxyalkylenated organosiloxane emulsifier, PEGylated organic siloxane emulsifiers, or a cross-linked organosiloxane emulsifiers. Although not specifically identified, some of the silicones listed below may be utilized as emulsifiers.

In some cases, the silicones, optionally, include or are chosen from siloxanes having an organo functional group, such as polyalkylsiloxanes, where at least one alkyl radical is different than methyl, for example organopolysiloxanes having the INCI name Stearyl Dimethicone, Cetyl Dimethicone or C26-28 Alkyl Dimethicone, or, for example, polyarylsiloxanes and polyarylalkylsiloxanes, for example organopolysiloxanes having the INCI name Phenyl Trimethicone, Trimethylsiloxyphenyl Dimethicone or Dimethylphenyl Dimethicone, or, for example, organopolysiloxanes having an organofunctional radical such as an aminopropyl, aminopropyl-aminoethyl, aminopropyl-aminoisobutyl radical, for example organopolysiloxanes having the INCI name Amodimethicone, or, for example, organopolysiloxanes having a polyethylene glycol or polyalkylene glycol radical, for example organopolysiloxanes having the INCI name PEG-12 Dimethicone, PEG/PPG-25,25-Dimethicone or Cetyl PEG/PPG-15/15 Butyl Ether Dimethicone.

In some instances, an amino-functionalized silicones is selected from compounds having the following formula:

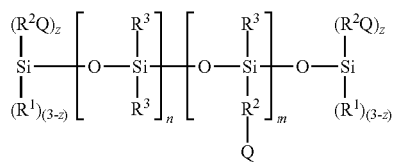

wherein each $R^1$ is independently selected from a $C_{1-30}$ alkyl group, a $C_{1-30}$ alkoxy group, a $C_{5-30}$ aryl group, a $C_{6-30}$ aralkyl group, a $C_{6-30}$ aralkyloxy group, a $C_{1-30}$ alkaryl group, a $C_{1-30}$ alkoxyaryl group, and a hydroxy group (preferably, each $R^1$ is independently selected from a $C_{1-30}$ alkyl group, a $C_{1-30}$ alkoxy group and a hydroxy group);

each $R^2$ is independently a divalent alkylene radical having one to ten carbon atoms (preferably, $R^2$ is a divalent alkylene radical having three to six carbon atoms);

each $R^3$ is independently selected from a $C_{1-30}$ alkyl group, a $C_{5-30}$ aryl group, a $C_{6-30}$ aralkyl group and a $C_{1-30}$ alkaryl group (preferably, each $R^3$ is independently selected from of a $C_{1-30}$ alkyl group);

Q is a monovalent radical selected from $-NR^4_2$ and $-NR^4(CH_2)_x NR^4_2$;

each $R^4$ is independently selected from a hydrogen and a $C_{1-4}$ alkyl group;

x is 2 to 6;

z is 0 or 1;

n is 25 to 3,000 (preferably, 25 to 2,000; more preferably, 25 to 1,000; most preferably 25 to 500); and m is 0 to 3,000 (preferably, 0 to 2,000; more preferably, 0 to 1,000; most preferably, 0 to 100);

with the proviso that at least 50 mol % of the total number of $R^1$ and $R^3$ groups are methyl and with the proviso that when m is 0, z is 1.

Preferred $R^1$ groups include methyl, methoxy, ethyl, ethoxy, propyl, propoxy, isopropyl, isopropoxy, butyl, butoxy, isobutyl, isobutoxy, phenyl, xenyl, benzyl, phenylethyl, tolyl and hydroxy. Preferred $R^2$ divalent alkylene radicals include trimethylene, tetramethylene, pentamethylene, $-CH_2CH(CH_3)CH_2-$ and $-CH_2CH_2CH(CH_3)CH_2-$. Preferred $R^3$ groups include methyl, ethyl, propyl, isopropyl, butyl, isobutyl, phenyl, xenyl, benzyl, phenylethyl and tolyl. Preferred $R^4$ groups include methyl, ethyl, propyl, isopropyl, butyl and isobutyl. When z is 0, the amino-functionalized silicine has only pendant amine functional substituents in the polymer chain. When z is 1, the amino-functional silicone may have only terminal amine functional substituents (e.g., m=0) or may have both terminal and pendant amine functional substituents in the polymer chain (e.g., m>0). Preferably, n+m is 50 to 1,000. More preferably, n+m is 50 to 750. Still more preferably, n+m is 50 to 500. Most preferably, n+m is 50 to 250.

In some instances, the amino-functionalized silicones are alkoxylated and/or hydroxylated amino silicones. Suitable alkoxylated and/or hydroxylated amino silicones may be selected from compounds of the following formula:

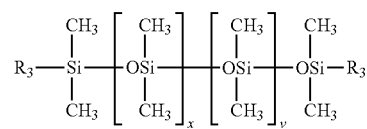

wherein $R_3$ is hydroxyl or $OR_5$, $R_5$ is a $C_1$ to $C_4$ alkyl group, $R_4$ is a group with structure according to the following formula:

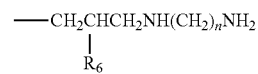

$R_6$ is a $C_1$ to $C_4$ alkyl, n is a 1 to 4, x is the same as "n" described above, and y is the same as "m" described above.

The silicone may be a polysiloxane corresponding to the following formula:

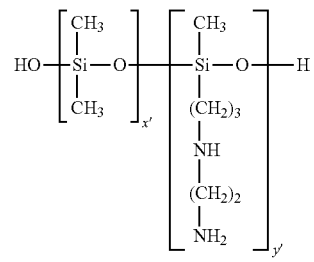

in which x' and y' are integers such that the weight-average molecular weight (Mw) is comprised between about 5000 and 500 000;

b) amino silicones corresponding to following formula:

in which:

G, which may be identical or different, designate a hydrogen atom, or a phenyl, OH or $C_1$-$C_8$ alkyl group, for example methyl, or $C_1$-$C_8$ alkoxy, for example methoxy, a, which may be identical or different, denote the number 0 or an integer from 1 to 3, in particular 0;

b denotes 0 or 1, and in particular 1;

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

R', which may be identical or different, denote a monovalent radical having formula —$C_qH_{2q}L$ in which q is a number ranging from 2 to 8 and L is an optionally quaternized amino group chosen from the following groups:

—NR"-Q-N(R")$_2$
—N(R")$_2$
—N+(R")$_3$A-
—N+H(R")$_2$A-
—N+H$_2$(R")A-
—N(R")-Q-N+R"H$_2$A-
—NR"-Q-N+(R")2HA-
—NR"-Q-N+(R")3A-, in which R", which may be identical or different, denote hydrogen, phenyl, benzyl, or a saturated monovalent hydrocarbon-based radical, for example a $C_1$-$C_{20}$ alkyl radical; Q denotes a linear or branched $CrH_{2r}$ group, r being an integer ranging from 2 to 6, preferably from 2 to 4; and A- represents a cosmetically acceptable ion, in particular a halide such as fluoride, chloride, bromide or iodide.

Another group of amino silicones corresponding to this definition is represented by silicones having the following formula:

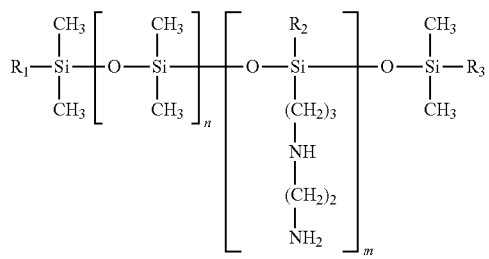

in which:

m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5;

$R_1$, $R_2$, $R_3$, which may be identical or different, represent a hydroxy or $C_1$-$C_4$ alkoxy radical, where at least one of the radicals $R_1$ to $R_3$ denotes an alkoxy radical.

The alkoxy radical is preferably a methoxy radical. The hydroxy/alkoxy mole ratio ranges preferably from 0.2:1 to 0.4:1 and preferably from 0.25:1 to 0.35:1 and more particularly equals 0.3:1. The weight-average molecular weight (Mw) of the silicone ranges preferably from 2,000 to 1,000,000, more particularly from 3,500 to 200,000.

Another group of amino silicones corresponding to this definition is represented by the following formula:

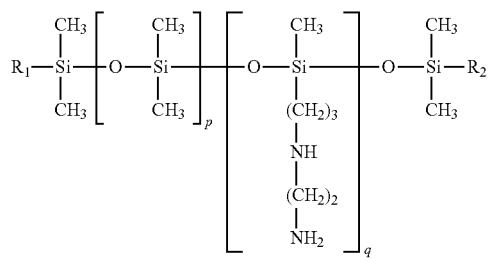

in which:

p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;

$R_1$, $R_2$, which may be the same or different, represent a hydroxy or $C_1$-$C_4$ alkoxy radical, where at least one of the radicals $R_1$ or $R_2$ denotes an alkoxy radical.

The alkoxy radical is preferably a methoxy radical. The hydroxy/alkoxy mole ratio ranges generally from 1:0.8 to 1:1.1 and preferably from 1:0.9 to 1:1 and more particularly equals 1:0.95.

Another group of amino silicones is represented by the following formula:

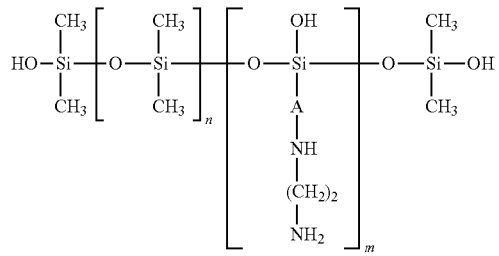

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably linear. The weight-average molecular weight (Mw) of these amino silicones ranges preferably from 2000 to 1 000 000 and even more particularly from 3500 to 200 000.

Another group of amino silicones is represented by the following formula:

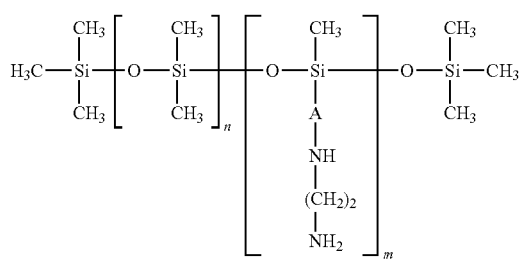

in which:

m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;

A denotes a linear or branched alkylene radical containing from 4 to 8 carbon atoms and preferably 4 carbon atoms. This radical is preferably branched. The weight-average molecular weight (Mw) of these amino silicones ranges preferably from 500 to 1 000 000 and even more particularly from 1000 to 200 000.

Another group of amino silicones is represented by the following formula:

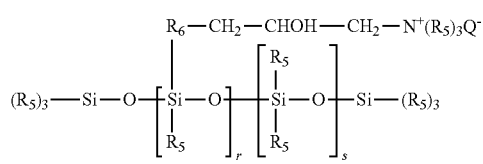

in which:

$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

Q- is an anion such as a halide ion, in particular chloride, or an organic acid salt (for example acetate);

r represents a mean statistical value from 2 to 20 and in particular from 2 to 8;

s represents a mean statistical value from 20 to 200 and in particular from 20 to 50. Such amino silicones are described more particularly in U.S. Pat. No. 4,185,087, which is incorporated herein in its entirety for all purposes.

A group of quaternary ammonium silicones is represented by the following formula:

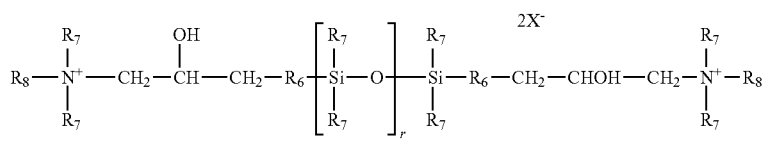

in which:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—NHCOR$_7$ radical;

X— is an anion such as a halide ion, in particular chloride, or an organic acid salt (for example acetate);

r represents a mean statistical value from 2 to 200 and in particular from 5 to 100. These silicones are described, for example, in European patent application no. 0530974, which is incorporated herein in its entirety for all purposes.

A group of quaternary ammonium silicones is represented by the following formula:

(J)

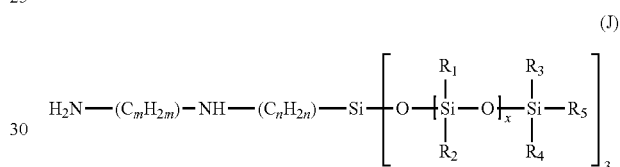

in which:

$R_1$, $R_2$, $R_3$ and $R_4$, which may be identical or different, denote a $C_1$-$C_4$ alkyl radical or a phenyl group;

$R_5$ denotes a $C_1$-$C_4$ alkyl radical or a hydroxyl group;

n is an integer ranging from 1 to 5;

m is an integer ranging from 1 to 5;

and in which x is chosen such that the amine number is between 0.01 and 1 meq/g;

multiblock polyoxyalkylenated amino silicones, of type (AB)n, A being a polysiloxane block and B being a polyoxyalkylenated block containing at least one amine group.

Said silicones are preferably constituted of repeating units having the following general formulae:

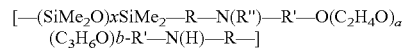

or alternatively

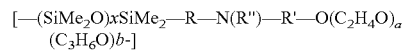

in which:

a is an integer greater than or equal to 1, preferably ranging from 5 to 200, more particularly ranging from 10 to 100;

b is an integer comprised between 0 and 200, preferably ranging from 4 to 100, more particularly between from 5 and 30;

x is an integer ranging from 1 to 10 000, more particularly from 10 to 5000;

R" is a hydrogen atom or a methyl;

R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —$CH_2CH_2CH_2OCH(OH)CH_2$— radical; preferentially R denotes a —$CH_2CH_2CH_2OCH(OH)CH_2$— radical;

R', which may be identical or different, represent a divalent linear or branched $C_2$-$C_{12}$ hydrocarbon-based radical, optionally including one or more heteroatoms such as oxygen; preferably, R' denotes an ethylene radical, a linear or branched propylene radical, a linear or branched butylene radical, or a —$CH_2CH_2CH_2OCH(OH)CH_2$— radical; preferentially R' denotes —$CH(CH_3)$—$CH_2$—. The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2. The weight-average molecular weight (Mw) of the silicone oil is preferably comprised between 5000 and 1,000,000, more particularly between 10,000 and 200,000.

The silicone may be selected from those having at least one quaternary ammonium group. Suitable non-limiting examples are quaternium 80, silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20 and silicone quaternium-21. Preferred are quaternium 80, silicone quaternium-16, silicone quaternium-18, silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-17, silicone quaternium-20 and silicone quaternium-21. More preferred are quaternium 80, silicone quaternium-16, silicone quaternium-18, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, and silicone quaternium-17. Preferred are quaternium 80, silicone quaternium-16, silicone quaternium-18, silicone quaternium-15, and mixtures thereof. In an embodiment, the one or more silicone oils of the present disclosure is a non-amino silicone oil such as a dimethicone.

Non-limiting examples of amino-functionalized silicones include bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof. In some instances, a particularly useful amino-functionalized silicone is bis-hydroxy/methoxy amodimethicone, wherein X is isobutyl and one of the R is OH and the other is $OCH_3$ in the above structure, also known as "Bis-Hydroxy/Methoxy Amodimethicone" and "3-[(2-aminoethyl)amino]-2-methylpropyl Me, di-Me, [(hydroxydimethylsilyl)oxy]- and Rmethoxydimethylsilyl)oxyHerminated." Bis-hydroxy/methoxy amodimethicone is commercially available under the tradename DOWSIL AP-8087 FLUID from The Dow Chemical Company. A non-limiting example of amodimethicone products containing amino silicones having structure (D) re sold by Wacker under the name BELSIL ADM 652, BELSIL ADM 4000 E, or BELSIL ADM LOG 1. A product containing amino silicones having structure (E) is sold by Wacker under the name FLUID WR 1300. Additionally or alternative, the weight-average molecular weight (Mw) of the silicone ranges preferably from 2,000 to 200,000, even more particularly 5,000 to 100,000 and more particularly from 10,000 to 50,000.

The silicone(s) in the skin treatment compositions of the instant disclosure are included in the form of a silicone emulsion comprising at least one silicone and at least one surfactants, for example, nonionic surfactants, cationic surfactants, amphoteric surfactants, anionic surfactants. The silicone emulsions can be nanoemulsions, microemulsions or macroemulsions. Suitable examples of nonionic surfactants are alkoxylated fatty alcohols or polyethylene glycol ethers of mixtures of C8-C30 fatty alcohols with an average of number of moles of ethylene oxide such as C11-15 Pareth-7, laureth-9, laureth-12, deceth-7, deceth-10, trideceth-6, trideceth-10, trideceth-12, or a mixture thereof. Suitable examples of amphoteric surfactants are cocamidopropyl betaine, coco-betaine, or a mixture thereof. Suitable examples of cationic surfactants are quaternary ammonium compounds such as behentrimonium chloride, cetrimoinium chloride, behentrimonium methosulfate, or a mixture thereof. Suitable examples of anionic surfactants are sulfate-based compounds such as further comprises up to 5 wt. % of a surfactant, for example, sodium (or ammonium) lauryl sulfate, sodium (or ammonium) laureth sulfate, or mixtures thereof.

Fatty Compound(s)

Examples of fatty compound(s) that may be incorporated into the skin treatment composition include fatty alcohol, a fatty ester, a fatty ether, a fatty acid, a wax, an oil, a derivative thereof, or a mixture thereof. Additional examples of fatty compounds that are worth mentioning include oils, mineral oil, alkanes (paraffins), fatty alcohol derivatives, fatty acid derivatives, esters of fatty alcohols, hydroxy-substituted fatty acids, waxes, triglyceride compounds, lanolin, and a mixture thereof. One or more fatty compounds(s) may be included in the skin treatment composition has an emulsifier. For example, the fatty compound may be a fatty alcohol that is capable of or is used for emulsifying another ingredient. Although not specifically identified, some of the fatty compounds listed below may be utilized as emulsifiers. Further examples of fatty compounds are discussed below.

(i) Fatty Ester(s)

The skin treatment compositions may include one or more fatty compound(s) that is a fatty ester. For example, the fatty compound(s) may be chosen from from dialkyl carbonates of formula: $R_1O(C=O)R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, preferably one or more fatty carbonates selected from C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a mixture thereof.

Additionally or alternatively, the fatty ester chosen from cetyl ester, purcellin oil (cetearyl octanoate), isopropyl myristate, isopropyl palmitate, $C_{12}$-$C_{15}$ alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, dicaprylyl carbonate, pentaerythritol esters, and a mixture thereof. Other fatty esters worth mentioning include polyglyceryl-10 oleate, polyglyceryl-10 dioleate, polyglyceryl-6 stearate, polyglyceryl-6 distearate, polyglyceryl-10 stearate, polyglyceryl-10 distearate, polyglyceryl-8 dipalmitate, polyglyceryl-10 dipalmitate, polyglyceryl-10 behenate, and polyglyceryl-12 trilaurate.

(ii) Fatty Alcohol(s)

Suitable fatty alcohols, if present, include those having a fatty group with a carbon chain of greater than 8 carbon atoms, 8 to 50 carbon atoms, 8 to 40 carbon atoms, 8 to 30 carbon atoms, 8 to 22 carbon atoms, 12 to 22 carbon atoms, or 12 to 18 carbon atoms, including all ranges and subranges therebetween. In some instances, the fatty group of the fatty alcohols has a carbon chain of 10 to 20 carbon atoms or 10 to 18 carbon atoms. The fatty alcohols may be chosen from polyethylene glycol ethers, such as those having a fatty alcohol group with a carbon chain of 12 to 16 or 12 to 14 carbon atoms.

The fatty alcohol portion is preferably hydrogenated (for example, stearyl, lauryl, cetyl, cetearyl); however, the fatty alcohol may contain one or more double bonds (for example, oleyl). Non-limiting examples of fatty alcohols include decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, and a mixture thereof. In some cases, the fatty alcohols comprise at least one of or may be chosen from myristyl alcohol, lauryl alcohol, cetyl alcohol, stearyl alcohol, cetearyl alcohol, isostearyl alcohol, oleyl alcohol, isotridecyl alcohol, and a mixture thereof.

The fatty alcohol may be saturated or unsaturated. Exemplary saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

Exemplary unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

The fatty alcohols may be alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or 15 to about 35 mores, including all ranges and subranges therebetween, of an alkylene oxide per mole of alkoxylated fatty alcohol.

As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

Additional fatty alcohol derivatives that may, optionally be suitable include methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

(iii) Fatty Ether(s)

The fatty compounds may be chosen from fatty ethers. For example, the skin treatment composition may include olyoxyethylene cetyl/stearyl ether, polyoxyethylene cholesterol ether, polyoxyethylene laurate or dilaurate, polyoxyethylene stearate or distearate, polyoxyethylene lauryl or stearyl ether, dicaprylyl ether, dicetyl ether distearyl ether, or a mixture thereof. Non-limiting examples of suitable polyoxyethylene fatty ethers include, but are not limited to, polyoxyethylene cetyl/stearyl ether, polyoxyethylene cholesterol ether, polyoxyethylene laurate or dilaurate, polyoxyethylene stearate or distearate, polyoxyethylene lauryl or stearyl ether, and mixtures thereof, wherein the polyoxyethylene head group ranges from about 2 to about 100 groups. In certain embodiments, the polyoxyethylene fatty ethers include polyoxyethylene stearyl ether, polyoxyethylene myristyl ether, polyoxyethylene lauryl ether having from about 3 to about 10 oxyethylene units and mixtures thereof.

(iv) Fatty Acid(s)

In some instances, the fatty compounds may be chosen from fatty acids, fatty acid derivatives, esters of fatty acids, hydroxyl-substituted fatty acids, and alkoxylated fatty acids. The fatty acids may be straight or branched chain acids and/or may be saturated or unsaturated. Non-limiting examples of fatty acids include diacids, triacids, and other multiple acids as well as salts of these fatty acids. For example, the fatty acid may optionally include or be chosen from lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Non-limiting examples of polyglycerol esters of fatty acids include those of the following formula:

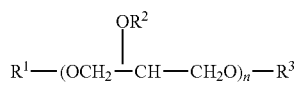

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

(v) Wax(es)

The fatty compounds may, in some instances, include or be chosen from one or more waxes. Non-limiting examples of waxes in this category include for example, synthetic wax, ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes (such as sunflower seed (*Helianthus annuus*), carnauba, candelilla, ouricury or japan wax or cork fibre or sugarcane waxes), or a mixture thereof.

(vi) Oil(s)

The skin treatment compositions include one or more oils. The oil component of the NLCs is typically has melting temperature of less than 45° C., a molecular weight of at least 190, and a solubility in water of no greater than 1 part in 99 parts of water.

Non-limiting examples of include, but are not limited to, natural oils, such as coconut oil; hydrocarbons, such as mineral oil and hydrogenated polyisobutene; esters, such as $C_{12}$-$C_{15}$ alkyl benzoate; diesters, such as propylene dipelarganate; and triesters, such as glyceryl trioctanoate. Further examples of oils that may, optionally, be included in the skin treatment compositions include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Additionally or alternatively, the oil may be selected from plant based and/or vegetable oils. Non-limiting examples of plant-based or vegetable oils include acai oil, almond oil, aloe vera oil, andiroba oil, annatto oil, avocado oil, babassu oil, borage oil, brazil nut oil, buriti oil, camelina oil, coffee oil, copaiba oil, emu oil, passion fruit oil, almond oil, ricinus communis (castor) seed oil, coconut oil, grapeseed oil, jojoba oil, macadamia nut oil, rose hip oil, ajwain oil, angelic root oil, anise oil, aragan oil, asafetida, balsam oil, basil oil, bay oil, bergamot oil, black pepper essential oil, buchu oil, birch oil, camphor, cannabis oil, caraway oil, cardamom seed oil, carrot seed oil, chamomile oil, calamus root oil, cinnamon oil, citronella oil, clary sage, clove leaf oil, coffee, coriander, costmary oil, cranberry seed oil, cubeb, cumin oil, cypress, cypriol, curry leaf, davana oil, dill oil, elecampane, eucalyptus oil, fennel seed oil, fenugreek oil, fir, frankincense oil, galangal, geranium oil, ginger oil, goldenrod, grapefruit oil, grapeseed oil, henna oil, helichrysum, horseradish oil, hyssop, Idaho tansy, jasmine oil, juniper berry oil, lavender oil, lemon oil, lemongrass, marjoram, melaleuca, lemon balm oil, mountain savory, mugwort oil, mustard oil, myrrh oil, myrtle, neem tree oil, neroli, nutmeg, orange oil, oregano oil, orris oil, palo santo, parsley oil, patchouli oil, perilla oil, pennyroyal oil, peppermint oil, petitgrain, pine oil, plum oil, ravensara, red cedar, roman chamomile, rose oil, rosehip oil, rosemary oil, rosewood oil, sandalwood oil, sassafras oil, savory oil, schisandra oil, spikenard, spruce, star anise oil, tangerine, tarragon oil, tea tree oil, thyme oil, tsuga oil, turmeric, valerian, vetiver oil, western red cedar, wintergreen, yarrow oil, ylang-ylang, and zedoary oil.

Non-limiting examples of liquid triglycerides and oils of plant origin include alexandria laurel tree oil, avocado oil, apricot stone oil, barley oil, borage seed oil, calendula oil, canelle nut tree oil, canola oil, caprylic/capric triglyceride castor oil, coconut oil, corn oil, cotton oil, cottonseed oil, evening primrose oil, flaxseed oil, groundnut oil, hazelnut oil, glycereth triacetate, glycerol triheptanoate, glyceryl trioctanoate, glyceryl triundecanoate, hempseed oil, jojoba oil, lucerne oil, maize germ oil, marrow oil, millet oil, neopentylglycol dicaprylate/dicaprate, olive oil, palm oil, passionflower oil, pentaerythrityl tetrastearate, poppy oil, propylene glycol ricinoleate, rapeseed oil, rye oil, safflower oil, sesame oil, shea butter, soya oil, soybean oil, sweet almond oil, sunflower oil, sysymbrium oil, syzigium aromaticum oil, tea tree oil, walnut oil, wheat germ glycerides and wheat germ oil.

Thickening Agent(s)

The skin treatment compositions described herein may, optionally, include a thickening agent. The amount of thickening agents can vary but is typically from about 0.01 to about 20 wt. %, based on the total weight of the skin treatment composition. In some instances, the amount of fatty compounds present in the skin treatment compositions is about 0.1 to 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 7 wt. %, about 0.1 to about 6 wt. %, about 0.1 to about 5 wt. %; about 0.5 to 20 wt. %, about 0.5 to about 18 wt. %, about 0.5 to about 16 wt. %, about 0.5 to about 14 wt. %, about 0.5 to about 12 wt. %, about 0.5 to about 10 wt. %, about 0.5 to about 8 wt. %, about 0.5 to about 7 wt. %, about 0.5 to about 6 wt. %, about 0.5 to about 5 wt. %; about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 2 to about 7 wt. %, about 2 to about 6 wt. %, about 2 to about 5 wt. %; about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 8 wt. %, about 3 to about 7 wt. %, about 3 to about 6 wt. %, about 3 to about 5 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. % about 4 to about 7 wt. %, about 4 to about 6 wt. %, about 4 to about 5 wt. %; about 5 to about 20 wt. %, about 5 to about 18 wt. %, about 5 to about 16 wt. %, about 5 to about 14 wt. %, about 5 to about 12 wt. %, about 5 to about 10 wt. %, or about 5 to about 8 wt. %, about 5 to about 7 wt. %, or about 5 to about 6 wt. %, including all ranges and sub-ranges therebetween, based on the total weight of the skin treatment composition.

The thickening agent(s) may be chosen from xanthan gum, guar gum, biosaccharide gum, cellulose, acacia seneca gum, sclerotium gum, agarose, pechtin, gellan gum, hyaluronic acid. Additionally, the one or more thickening agents may include polymeric thickening agents selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some cases, the skin treatment composition includes ammonium polyacryloyldimethyl taurate and/or sodium polyacrylate. Suitable thickening agents may be found in U.S. patent application Ser. No. 16/731,654, which is incorporated herein, in its entirety for all purposes.

Many thickening agents are water-soluble, and increase the viscosity of water or form an aqueous gel when the skin treatment composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water.

Particular types of thickening agents that may be mentioned include the following:

One or more thickening agents can optionally be included in the skin treatment compositions of the instant disclosure. Thickening agents may be referred to as "thickeners" or "viscosity modifying agents." Thickening agents are typically included to increase the viscosity of the skin treatment compositions. Nonetheless, in some instances, certain thickening agents provide additional, surprising benefits to the skin treatment compositions. Non-limiting examples of thickening agents include polyacrylate crosspolymers or crosslinked polyacrylate polymers, cationic acrylate copolymers, anionic acrylic or carboxylic acid polymers, polyacrylamide polymers, polysaccharides such as cellulose derivatives, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a mixture thereof. Particular types of thickening agents that may be mentioned include the following:

Carboxylic Acid or Carboxylate based
Homopolymer or co-Polymer, which can be Linear
or Crosslinked These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., $C_1$-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is available in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw material known under the tradename of SIMULQUAT HC 305 from Seppic.

In certain embodiments, the carboxylic acid or carboxylate polymer thickening agents useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

Celluloses

Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water-soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).

Polyvinylpyrrolidone (PVP) and co-Polymers

Non-limiting examples include Polyvinylpyrrolidone (PVP), Polyvinylpyrrolidone (PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commercially available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.

Sucrose Esters

Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

Polyglyceryl Esters

Non-limiting polyglycerol esters of fatty acids (polygylceryl esters) include those of the following formula:

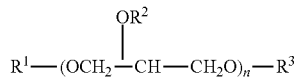

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

Gums

Non-limiting examples of gums include gum arabic, tragacanth gum, karaya gum, guar gum, gellan gum, tara gum, locust bean gum, tamarind gum, xanthan gum, locust bean gum, Seneca gum, sclerotium gum, gellan gum, etc.

pH Adjuster(s)

The skin treatment composition may include one or more pH adjusters to increase or decrease the overall pH of the skin treatment composition. For example, one or more acids may be included to decrease the pH of the skin treatment composition. Examples of suitable acids for decreasing the pH of the skin treatment composition include, but are not limited to, citric acid, acetic acid, and the like. The skin treatment composition may include one or more bases, such as sodium hydroxide, potassium hydroxide and the like, to increase the pH of the skin treatment composition. Additional or alternative acids and bases that are suitable for adjusting the pH of the skin treatment composition are readily known to one of ordinary skill in the art.

The amount of the pH adjuster in the skin treatment composition may be based on the desired pH of the final skin treatment composition and/or product. For example, the skin treatment composition may have an amount of pH adjusters such that the pH of the composition is about 3 to about 7, preferably about 3.5 to about 6.5, preferably about 3.5 to about 6, or preferably about 3.5 to about 5.5.

The amount of the pH adjuster in the skin treatment composition may be based on the desired pH of the final skin treatment composition and/or product. For example, the total amount of the pH adjuster may range from about 0.05 to about 20 wt. %, based on the total weight of the skin treatment composition. In some instances, the total amount of pH adjuster is from about 0.05 to about 15 wt. %, about 0.1 to about 10 wt. %, or about 0.12 to about 5 wt. %, including ranges and sub-ranges therebetween, based on the total weight of the skin treatment composition.

Chelating Agent(s)

The skin treatment composition may, optionally, include chelating agents. The amount of chelating agent present in the skin treatment composition may be, e.g., about 0.01 to about 20 wt. %, about 0.01 to about 15 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %; about 0.1 to about 20 wt. %, about 0.1 to about 15 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 20 wt. %, about 0.25 to about 15 wt. %, about 0.25 to about 10 wt. %, about 0.25 to about 8 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 20 wt. %, about 0.5 to about 15 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 20 wt. %, about 0.75 to about 15 wt. %, about 0.75 to about 10 wt. %, about 0.75 to about 8 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 20 wt. %, about 1 to about 15 wt. %, about 1 to about 10 wt. %, about 1 to about 8 wt. %, about 1 to about 6 wt. %, about 1 to about 5 wt. %, about 1 to about 4 wt. %, about 1 to about 3 wt. %, or about 1 to about 2 wt. %, including ranges and subranges therebetween, based on the total weight of the skin treatment composition.

Non-limiting examples of chemical chelating agents include aminotrimethyl phosphonic acid, β-alanine diacetic acid, cyclodextrin, cyclohexanediamine tetracetic acid, diethylenetriamine pentamethylene phosphonic acid, diethanolamine N-acetic acid, ethylene diamine tetracetic acid (EDTA or $YH_4$) and its sodium ($YH_3Na$, $Y_2H_2Na_2$, $YHNa_3$ and $YNa_4$), potassium ($YH_3K$, $Y_2H_3K_3$ and $YK_4$), calcium disodium, and diammonium salts and its salts with triethanolamine (TEA-EDTA), etidronic acid, galactanic acid, hydroxyethyl ethylenediamine tetracetic acid (HEDTA) and its trisodium salt, gluconic acid, glucuronic acid, nitrilotriacetic acid (NTA) and its trisodium salt, pentetic acid, phytic acid, ribonic acid, diammonium citrate, disodium azacycloheptane diphosphonate, disodium pyrophoshate, hydroxypropyl cyclodextrin, methyl cyclodextrin, pentapotassium triphosphate, pentasodium aminotrimethylene phosphonate, pentasodium ethylenediamine tetramethylene phosphonate, pentasodium pentetate, pentasodium triphosphate, potassium citrate, potassium EDTMP, sodium EDTMP, sodium chitosan methylene phosphonate, sodium hexametaphosphate, sodium metaphosphate, potassium polyphosphate, sodium polyphosphate, sodium trimetaphosphate, sodium dihydroxyethylglycinate, potassium gluconate, sodium gluconate, sodium glucopeptate, sodium glycereth-1 polyphosphate, tetrapotassium pyrophosphate, triethanolamine polyphosphate (TEA), tetrasodium pyrophosphate, trisodium phosphate, potassium triphosphonomethylamine oxide, sodium metasilicate, sodium phytate, sodium polydimethylglycinophenolsulfonate, tetrahydroxyethyl ethylene diamine, tetrahydroxypropyl ethylene diamine, tetrapotassium etidronate, tetrasodium etidronate, tetrasodium iminodisuccinate, trisodium ethylenediamine disuccinate, ethanolamine N,N-diacetic acid, disodium acetate, dimercaprol, deferoxamine, Zylox, and/or iron chelating agent disclosed and claimed in the international patent application WO 94/61338, which is incorporated herein in its entirety for all purposes. Examples of biological chelating agents include metallothionein, transferrin, calmodulin, and sodium chitosan methylene phosphonate. In at least one instance, the chelating agent is trisodium ethylenediamine disuccinate.

Preservative(s)

Preservatives may be included in the skin treatment composition in an amount typically from about 0.01 to about 20 wt. %, about 0.01 to about 18 wt. %, about 0.01 to about 16 wt. %, about 0.01 to about 14 wt. %, about 0.01 to about 12 wt. %, about 0.01 to about 10 wt. %, about 0.01 to about 8 wt. %, about 0.01 to about 7 wt. %, about 0.01 to about 6 wt. %, about 0.01 to about 5 wt. %; about 0.1 to about 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 7 wt. %, about 0.1 to about 6 wt. %, about 0.1 to about 5 wt. %; about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. %, or about 4 to about 7 wt. %, including all ranges and sub-ranges therebetween, based on the total weight of the skin treatment composition. Non-limiting examples of preservatives include sodium benzoate, potassium sorbate, phenoxyethanol, salicylic acid, tocopherol, chlorphenesin, BHT, disodium EDTA, pentaerythrityl tetra-di-t-butyl hydroxyhydrocinnamate, and mixtures thereof.

Water

The skin treatment composition may include 10 wt. % or more of water. For example, the amount of water present in the skin treatment composition may be about 10 wt. % or more, about 15 wt. % or more, about 20 wt. % or more, about 25 wt. % or more, about 30 wt. % or more, about 35 wt. % or more, about 40 wt. % or more, about 45 wt. % or more, about 50 wt. % or more, about 55 wt. % or more, about 60 wt. % or more, about 65 wt. % or more, about 70 wt. % or more, about 75 wt. % or more, about 80 wt. % or more, about 85 wt. % or more, or about 90 wt. % or more, based on the total weight of the skin treatment composition. Additionally or alternatively, the skin treatment compositions may have about 95 wt. % or less, about 90 wt. % or less, about 85 wt. % or less, about 80 wt. % or less, about 75 wt. % or less, about 70 wt. % or less, about 65 wt. % or less, about 60 wt. % or less, about 55 wt. % or less, about 50 wt. % or less, about 45 wt. % or less, about 40 wt. % or less, about 35 wt. % or less, about 30 wt. % or less, about 25 wt. % or less, about 20 wt. % or less, about 15 wt. % or less, about 10 wt. % or less, about 5 wt. % or less, about 3 wt. % or less, about 2 wt. % or less, or about 1 wt. % or less, based on the total weight of the skin treatment composition. In some embodiments, the skin treatment compositions have an amount of water based on the above lower and upper limits, such as, e.g., about 40 to about 90 wt. %, about 45 to about 80 wt. %, about 48 to about 75 wt. %, including ranges and subranges therebetween, based on the total weight of the skin treatment composition. Although the skin treatment compositions may be aqueous, in certain embodiments, the skin treatment compositions are free of water (anhydrous) or substantially free of water (substantially anhydrous).

In some embodiments, the skin tightening composition may be devoid of mono-alcohol. Those of skill in the art will appreciate that mono-alcohol may be present in a composition via its presence in one or more of the ingredients; thus, in some embodiments the skin treatment composition may be substantially free of alcohol. For example, alcohol may be present in the skin treatment composition at a concentration that does not exceed 5 wt. %, and in some instances is present not more than 3 wt. %, and in some instances is present not more than 1 wt. %, based on the total weight of the skin treatment composition.

The skin treatment composition may, optionally, include about 10 wt. % or less of miscellaneous ingredients, based on the total weight of the skin treatment composition. Non-limiting examples of miscellaneous ingredients include active ingredients, pH adjusters, preservatives, salts, chelating agent, colorants, salts, antimicrobial agents, fragrances, vitamins, pearlescent agents, odor absorbers, coloring materials, essential oils, fruit extracts, and combinations thereof. One or more of the foregoing miscellaneous ingredients may be excluded from embodiments of the disclosure. The amount of miscellaneous ingredients may be about 10 wt. % or less, about 9 wt. % or less, about 8 wt. % or less, about 7 wt. % or less, about 6 wt. % or less, about 5 wt. % or less, about 4 wt. % or less, about 3 wt. % or less, about 2 wt. % or less, or about 1 wt. % or less, based on the total weight of the skin treatment composition.

Embodiments of the Disclosure

In accordance with an embodiment of the disclosure, provided is a method for improving skin comprising:
reducing the barrier function of skin, e.g. by applying a laser procedure, a microneedle procedure, a cryotherapy procedure, a radiofrequency microneedle procedure, or a combination thereof; and
applying a skin treatment composition to the skin, the skin treatment composition comprising:
(i) about 0.1 to about 25 wt. %, preferably about 0.1 to about 16 wt. %, more preferably about 0.1 to about 10 wt. % of acetyl trifluoromethylphenyl valylglycine;
(ii) about 0.5 to about 30 wt. %, preferably about 0.5 to about 25 wt. %, more preferably about 5 to about 20 wt. %, of a polyol, wherein the polyol is chosen from ethylene glycol, propylene glycol, butylene glycol, hexylene glycol, pentylene glycol, diethylene glycol, dipropylene glycol, 1,3 propanediol, glycerin, polyethylene glycols, and a mixture thereof;
(iii) about 0.1 to about 30 wt. %, preferably about 0.5 to about 25 wt. %, more preferably about 15 to about 25 wt. %, of a silicone, fatty compound, or a mixtures thereof, wherein the silicone, fatty compound or a mixture thereof comprises a silicone chosen from lauryl peg-9 polydimethylsiloxyethyl dimethicone, dimethylsiloxane, poly dimethylsiloxane, polydimethylsiloxane, dimethicone, acrylate/dimethicone polymer, and mixtures thereof and/or a fatty compound chosen from a fatty alcohol, a fatty ester, a fatty ether, a fatty acid, a hydrocarbon oil, derivatives thereof, or mixtures thereof,
wherein the skin treatment composition is an emulsion, and all weight percentages are based on the total weight of the skin treatment composition.

The terms "comprising," "having," and "including" are used in their open, non-limiting sense. The terms "a" and "the" are understood to encompass the plural as well as the singular. The compositions and methods of the present disclosure can comprise, consist of, or consist essentially of the essential elements and limitations of the disclosure described herein, as well as any additional or optional ingredients, components, or limitations described herein or otherwise useful.

All percentages, parts and ratios herein are based upon the total weight of the compositions of the present disclosure, unless otherwise indicated. All ranges and values disclosed herein are inclusive and combinable. The expression "inclusive" for a range of concentrations means that the limits of the range are included in the defined interval. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

As used herein, the expression "at least one" is interchangeable with the expression "one or more" and thus includes individual components as well as mixtures/combinations.

The term "substantially free" or "essentially free" as used herein means that there is less than about 5% by weight of a specific material added to a composition, based on the total weight of the compositions. Nonetheless, the compositions may include less than about 2 wt. %, less than about 1 wt. %, less than about 0.5 wt. %, less than about 0.1 wt. %, less than 0.01 wt. %, or none of the specified material.

The term "active material" as used herein with respect to the percent amount of an ingredient or raw material, refers to 100% activity of the ingredient or raw material.

Throughout the disclosure, the term "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included. The salts referred to throughout the disclosure may include salts having a counter-ion such as an alkali metal, alkaline earth metal, or ammonium counter-ion. This list of counter-ions, however, is non-limiting.

"Volatile", as used herein, means having a flash point of less than about 100° C. "Non-volatile", as used herein, means having a flash point of greater than about 100° C.

The term "polymers," as defined herein, include homopolymers and copolymers formed from at least two different types of monomers.

The term "INCI" is an abbreviation of International Nomenclature of Cosmetic Ingredients, which is a system of names provided by the International Nomenclature Committee of the Personal Care Products Council to describe personal care ingredients.

All components and elements positively set forth in this disclosure can be negatively excluded from the claims. In other words, the compositions (nanoemulsions) of the instant disclosure can be free or essentially free of all components and elements positively recited throughout the instant disclosure.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or as only the fatty compound (the single fatty acid does not serve as both the nonionic surfactant and the fatty compound).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

EXAMPLES

Implementation of the present disclosure is provided by way of the following examples. The examples serve to illustrate the technology without being limiting in nature.

Example 1

Example Compositions

Three non-limiting, exemplary composition (Example Compositions 1-3) were produced according to aspects of the disclosure. Example Compositions 1 and 2 were formulated to form oil-in-water emulsions and Example Composition 3 was formulated to form a water-in-oil emulsion.

| Example Composition 1 (Ex. 1) | | |
|---|---|---|
| | US INCI ingredient names | Wt. % |
| Acetyl trifluoromethylphenyl valylglycine | ACETYL TRIFLUOROMETHYLPHENYL VALYLGLYCINE | 10 |
| Silicone | CETYL PEG/PPG-10/1 DIMETHICONE, PEG/PPG-18/18 DIMETHICONE, DIMETHICONE, C30-45 ALKYL DIMETHICONE, and DIMETHICONOL | 15 |
| Emollient | PENTAERYTHRITYL TETRAETHYLHEXANOATE | 2 |
| Fatty compound | ETHYLHEXYL PALMITATE and ISOHEXADECANE | 5 |
| Polyol | GLYCERIN, CAPRYLYL GLYCOL, and BUTYLENE GLYCOL | 8 |
| Skin Active Agents | *CENTELLA ASIATICA* EXTRACT, SODIUM PALMITOYL PROLINE, *NYMPHAEA ALBA* FLOWER EXTRACT, and SODIUM CARBOXYMETHYL BETA-GLUCAN | 1 |
| Miscellaneous (preservatives, bulking agent, pH adjusters, and/or the like) | PHENOXYETHANOL, SODIUM BENZOATE, MAGNESIUM SULFATE, and CITRIC ACID | 1 |
| Water | DEIONIZED WATER | QS to 100 |

| Example Composition 2 (Ex. 2) | | |
|---|---|---|
| | US INCI ingredient names | Wt. % |
| Acetyl trifluoromethyl- phenyl valylglycine | ACETYL TRIFLUOROMETHYLPHENYL VALYLGLYCINE | 1 |
| Silicone | LAURYL PEG-9 POLYDIMETHYLSILOXYETHYL DIMETHICONE, DIMETHICONE, DIMETHICONE/VINYL DIMETHICONE CROSSPOLYMER, DIMETHICONE CROSSPOLYMER, DIMETHICONE/PEG-10/15 CROSSPOLYMER, DIMETHICONOL, and ACRYLATES/DIMETHICONE COPOLYMER | 24 |
| Polyol | GLYCERIN and CAPRYLYL GLYCOL | 15 |
| Skin Active Agents | PANTHENOL | 5 |
| Miscellaneous (preservatives, bulking agent, and/or the like) | PHENOXYETHANOL and SODIUM CITRATE | 1 |
| Water | WATER | QS to 100 |

| Example Composition 3 (Ex. 3) | | |
|---|---|---|
| | US INCI ingredient names | Wt. % |
| Acetyl trifluoromethyl- phenyl valylglycine | ACETYL TRIFLUOROMETHYLPHENYL VALYLGLYCINE | 1 |
| Fatty Compounds | BEHENYL ALCOHOL, GLYCERYL STEARATE CITRATE, SODIUM STEAROYL GLUTAMATE, CETYL ESTERS, BEESWAX/ *CERA ALBA*, *BUTYROSPERMUM PARKII* (SHEA) BUTTER/*BUTYROSPERMUM PARKII* BUTTER, POLYGLYCERYL-6-DISTEARATE, JOJOBA ESTERS, CETYL ALCOHOL, POLYGLYCERYL-3-BEESWAX, DICAPRYLYL ETHER, *LIMNANTHES ALBA* (MEADOWFOAM) SEED OIL/*LIMNANTHES ALBA* SEED OIL, ARACHIDYL ALCOHOL, BEHENYL ALCOHOL, and ARACHIDYL GLUCOSIDE | 24 |
| Polyols | GLYCERIN, PROPANEDIOL, PENTYLENE GLYCOL, and CAPRYLYL GLYCOL | 14 |
| Thickening Agents | HYDROXYPROPYL STARCH PHOSPHATE and XANTHAN GUM | 1 |
| Skin Active Agents | SODIUM HYALURONATE, CAPRYLOYL SALICYLIC ACID, and COCO-CAPRYLATE/CAPRATE | 2 |
| pH Adjuster | SODIUM HYDROXIDE | <1 |
| Water | WATER/AQUA | QS to 100 |

Example 2

In Vitro Evaluation of Composition 4

The benefits of applying the Composition 4 to skin after a procedure that reduces the barrier function of skin was evaluated in vitro using samples generated by the EPISKIN™ group. Composition 4 comprised 0.5 wt. % of acetyl trifluoromethylphenyl valylglycine and 2 wt. % ethanol with the remainder being water, with all weight percentages based on the total weight of the formulation. A comparative composition (Comparative Composition A) containing transforming growth factor alpha ("TGF-α") was also evaluated as a comparison to the Composition 4.

Specifically, a fractional laser procedure that is typical of laser resurfacing procedures was applied to the in vitro skin samples. The in vitro skin samples were characterized using non-invasive imaging analysis to determine the wound morphology of the in vitro skin samples. The kinetics and quantification of wound healing after the laser treatment was evaluated using optical coherence tomography (OCT). The optical measurements were performed at seven time points over the culture period. This was achieved using an OCT system produced by Thorlabs (Newton, N.J., USA) with an axial resolution of 8 μm.

Composition 4 and Comparative Composition A were applied by adding 10 uL onto in vitro skin samples after the fractional laser procedure. The in vitro skin samples were imaged after the application of Composition 4 and Comparative Composition A on the day of the fractional laser procedure, 2 days after the fractional laser procedure, and 4 days after the fractional laser procedure. 10 uL samples of Composition 4 and Comparative Composition A were applied daily during the course of this experiment. Images of the in vitro skin samples at 0 day, 2 days, and 4 days after the fractional laser procedure are shown in FIG. 1. As seen in FIG. 1, both Composition 4 and Comparative Composition A improved the keratinocyte invasion into the dermal injury.

Figure 2:
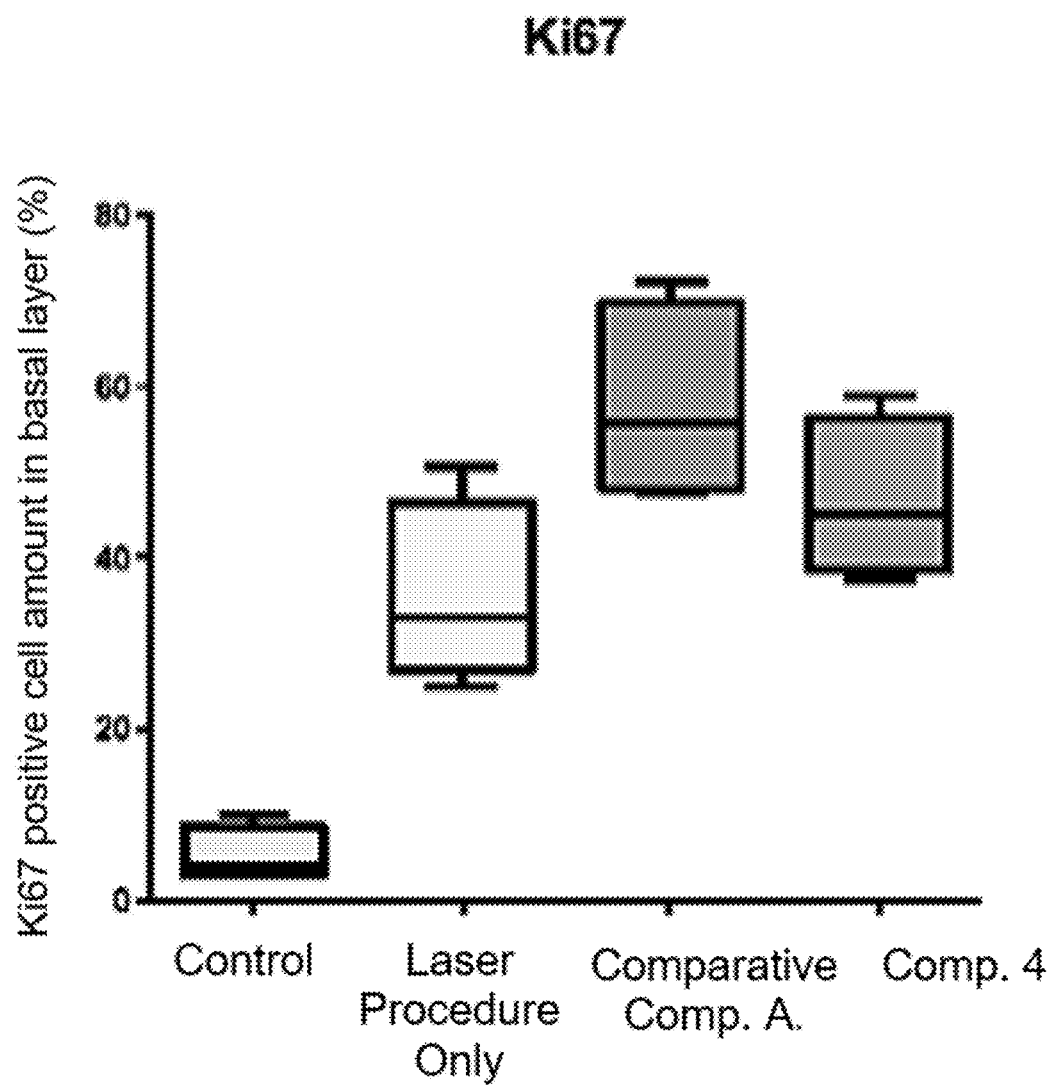
FIG. 2 is a bar graph showing the amount of Ki67 positive cells in the basal layer of in vitro skin samples after application of a comparative composition or a non-limiting exemplary composition according to aspects of the disclosure.

The in vitro skin samples were also evaluated to assess cell proliferation. Specifically, the Ki67 protein was marked and imaged to determine the amount of Ki67 positive cells in the basal layer of the in vitro skin samples. The reconstructed skin models were fixed in neutral formalin solution. The models were embedded and paraffin sectioned. The sections then underwent standard haematoxylin and eosin staining. The cryosection tissue slices were immunolabeled using the following primary antibodies: anti-filaggrin (FLG01, Thermo Fisher Scientific, Waltham, Mass., USA), and anti-Ki67 (P05211CN_02, Dako, Glostrup, Denmark). Photomicrographs were captured using an Eclipse Ti fluorescence microscope, commercially available from Nikon Instruments Inc. Statistical analyses were performed using GraphPad Prism. FIG. 2 is a bar graph showing the amount of Ki67 positive cells in the basal layer of the in vitro skin samples. Composition 4 and Comparative Composition A both lead to an increase in Ki67 positive cells in the basal layer as compared to the in vitro skin samples that received the fractional laser procedure without Composition 4 or Comparative Composition A. Comparative Composition A lead to more Ki67 positive cells than Composition 4.

Figure 3:
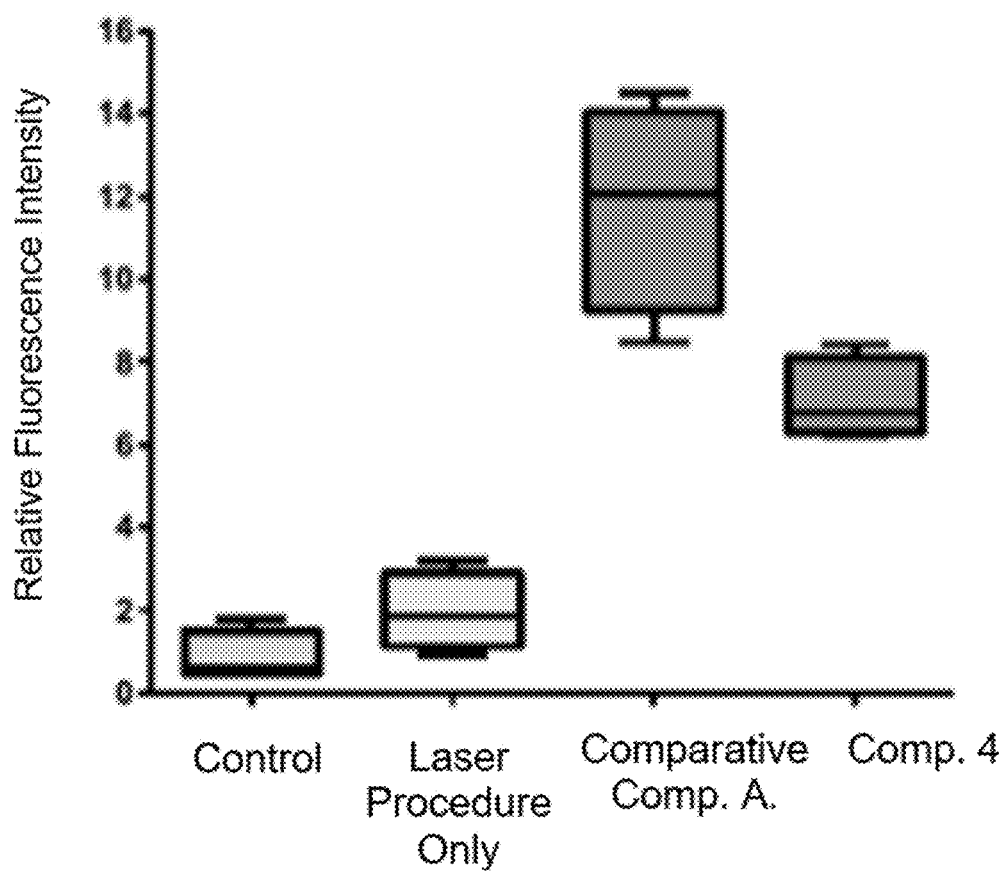
FIG. 3 is a bar graph showing the relative fluorescence intensity, indicating the amount of filaggrin in in vitro skin samples after application of a comparative composition or a non-limiting exemplary composition in accordance with aspects of the disclosure.

The in vitro skin samples were assessed for increased filaggrin expression by fluorescence marking of the filaggrin protein and subsequent imaging, using procedures similar to those discussed above. FIG. 3 is a bar graph showing the relative fluorescence intensity, indicating the amount of filaggrin in the in vitro skin samples. The benefits of applying Composition 4 after the fractional laser procedure is observed as the group treated with Composition 4 showed accelerated wound closure (reduced dermis inclusion volume) on day 4 as compared to the laser control group (which did not receive any skin treatment composition). The group treated with Composition 4 showed significantly higher filaggrin expression compared to both the control and laser control groups. This model demonstrated that the application of acetyl trifluoromethylphenyl valylglycine after the fractional laser procedure is beneficial as the wound exhibited enhanced regeneration of the epidermis.

Example 3

Ex Vivo Evaluation of Composition 4

Composition 4 was evaluated using an ex vivo skin model to assess cellular growth and particular regeneration of the barrier function of the skin. The ex vivo skin samples were obtained from EPISKIN™. The stratum corneum layer of the ex vivo skin samples was removed using a tape strip and confirmed under a microscope. After removal of the stratum corneum layer, Composition 4 and a commercially available product ("Comparative Composition B"), containing petrolatum, mineral oil, ceresin, lanolin alcohol, panthenol, glycerin, and bisabolol, were applied once a day to respective ex vivo skin samples. The ex vivo skin samples were stained and imaged using a microscope to assess the regrowth of the stratum corneum layer.

Figure 4:
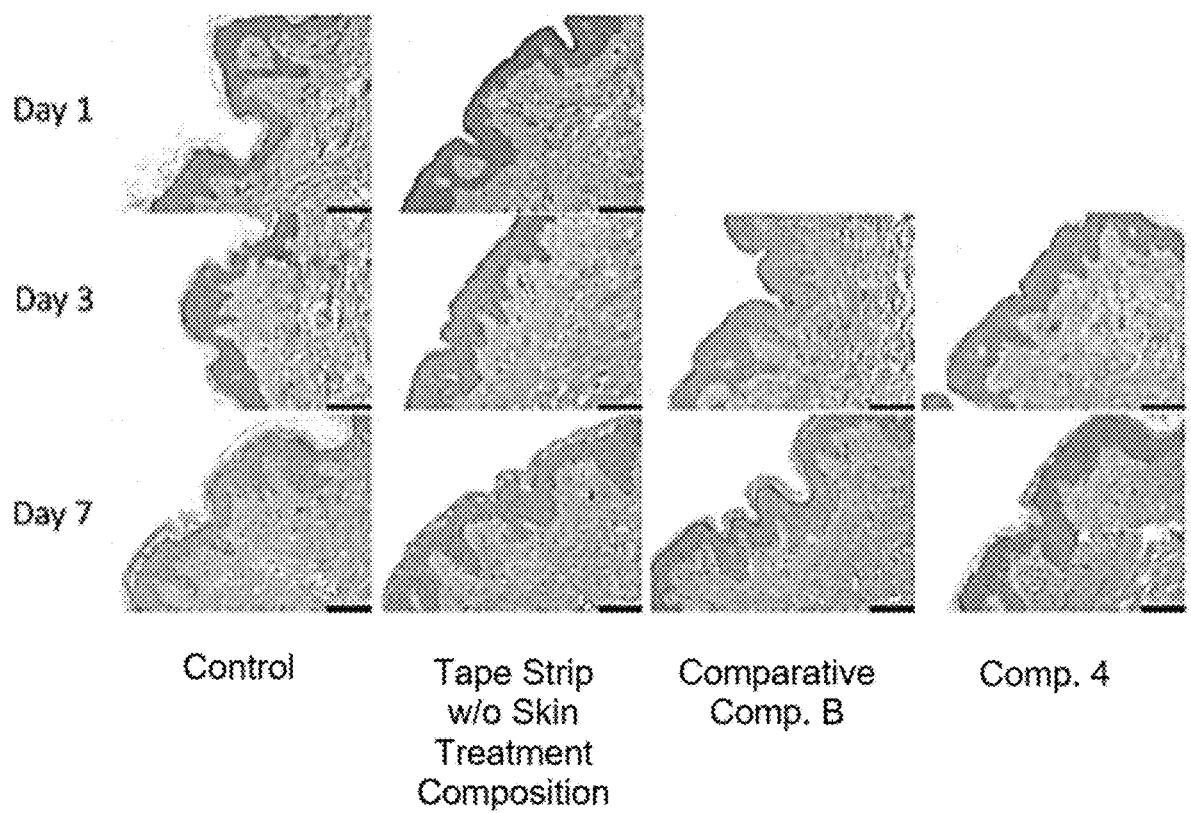
FIG. 4 is images of ex vivo skin samples 1 day, 3 days, and 7 days after removal of the stratum corneum according to aspects of the disclosure.

In particular, the skin explants were processed for haematoxylin and eosin staining (commercially available from Reveal Biosciences, San Diego, Calif.). Immunohistochemical staining was performed using a Leica Bond automated immunostainer (commercially available from Reveal Biosciences, San Diego, Calif.). Tissue samples were embedded as formalin-fixed paraffin embedded (FFPE) blocks. Heat induced antigen retrieval was performed using Leica Bond Epitope Retrieval Buffer and endogenous peroxidase was blocked for 20 minutes. Non-specific antibody binding was blocked for 30 minutes using Novolink Protein Block and sections were incubated with the primary antibodies Mouse Monoclonal to Anti-Filaggrin (available from Thermofisher, Waltham, Mass.) and Rabbit Polyclonal to Anti-Transglutaminase 3 (available from Thermofisher, Waltham, Mass.). Anti-Filaggrin and Anti-Transglutaminase 3 was detected using Novocastra Bond Refine Polymer Detection and visualized with 3'3 diaminobenzidine (DAB). All sections were then counterstained with a hematoxylin nuclear stain and imaged with a fluorescent microscope, specifically a Leica DM500 microscope produced by Leica Microsystems. Staining intensity was determined by calculating the optical density of staining using computer software, specifically MATLAB R2020a. FIG. 4 provides images of the ex vivo skin samples 1 day, 3 days, and 7 days after removal of the stratum corneum.

Figure 5:
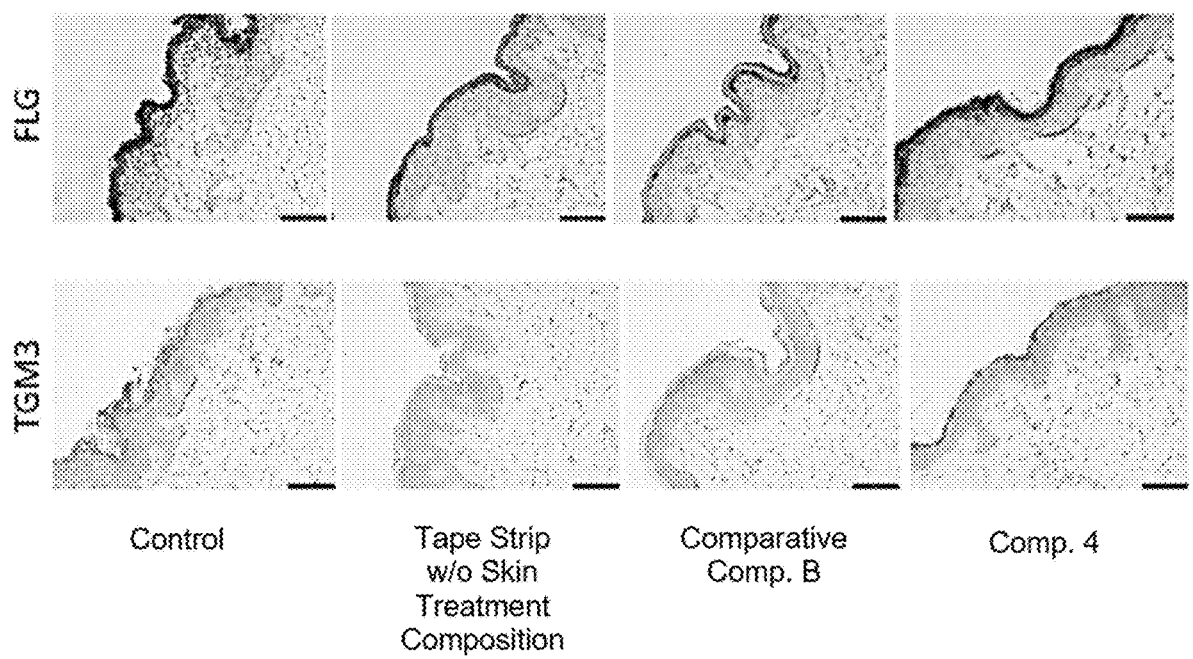
FIG. 5 is images of the amount of Filaggrin and Transglutaminase 3 in ex vivo skin samples after application of a comparative composition or a non-limiting exemplary composition in accordance with aspects of the disclosure.

The amount of Filaggrin ("FLG") and Transglutaminase 3 ("TGM3"), which are important biomarkers related to skin barrier function, was assessed for the ex vivo skin samples. The amount of FLG and TGM3 is indicative of an improvement of the barrier function of the ex vivo skin samples. FIG. 5 provides images of the FLG and TGM3 of the ex vivo skin samples. The amount of Filaggrin and Transglutaminase 3 was assessed using procedures similar to those discussed above.

FIG. 5 provides images of the skin barrier 7 days removal of the stratum corneum layer of the ex vivo skin samples. As seen in FIG. 5, Composition 4 provided a more mature regenerated skin barrier. It also appears that the Composition 4 increased TGM3 expression, which indicates stratum corneum layer and skin barrier stimulation. The tape-stripped skin that was treated with Composition 4 showed enhanced filaggrin expression as compared to the control and the tape-stripped skin that was treated with Composition B. Additionally, the tape-stripped skin that was treated with Composition 4 demonstrated an improvement in the keratinization and upper terminal differentiation process in the skin. In comparison, Composition B did not demonstrate improvement in terminal differentiation marker expression or lipid structure reformation. Accordingly, it is believed that certain skin treatment compositions containing acetyl trifluoromethylphenyl valylglycine can be used following skin treatment procedures to restore a mature and fortified barrier.

Example 4

Wound Recovery and Epithelial Confluence

Twenty two volunteers between the ages of 18 and 40 years old having skin types of Fitzpatrick IV received six wounds on each volar arm using 5 watts of $CO_2$ followed by 1.7 $J/cm^2$ of erbium. The wounds were representative of certain ablative laser treatments. The volunteers either received a composition comprising Example Composition 1, Composition 5, Comparative Composition B, or did not receive any skin treatment composition (control). Composition 5 had the same formula as Example Composition 1, except for Composition 5 included an additional 10 wt. % of water instead of the acetyl trifluoromethylphenyl valylglycine. The volunteers were evaluated for 56 days.

Figure 14:
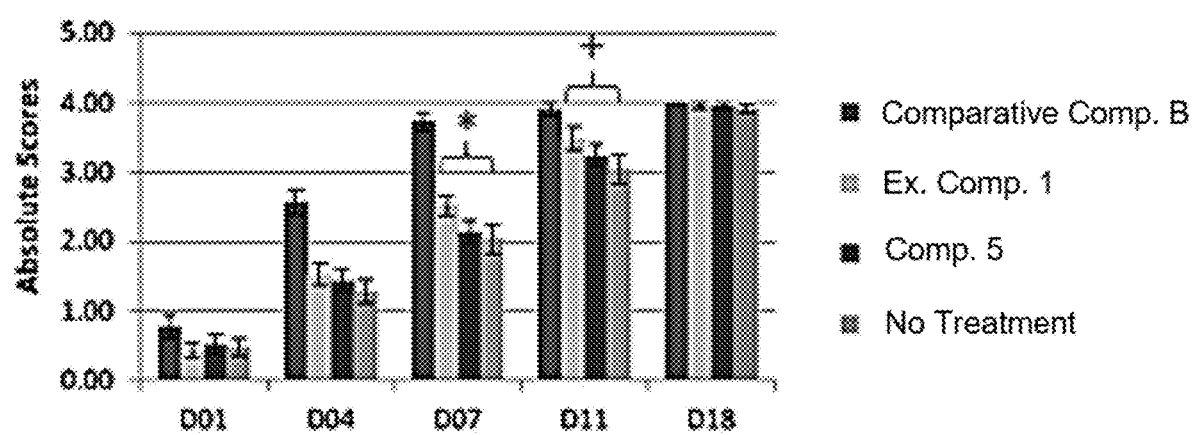
FIG. 14 is a bar graph illustrating absolute scores after receiving an application of a non-limiting exemplary skin treatment composition or a comparative composition according to aspects of the disclosure.
Figure 15:
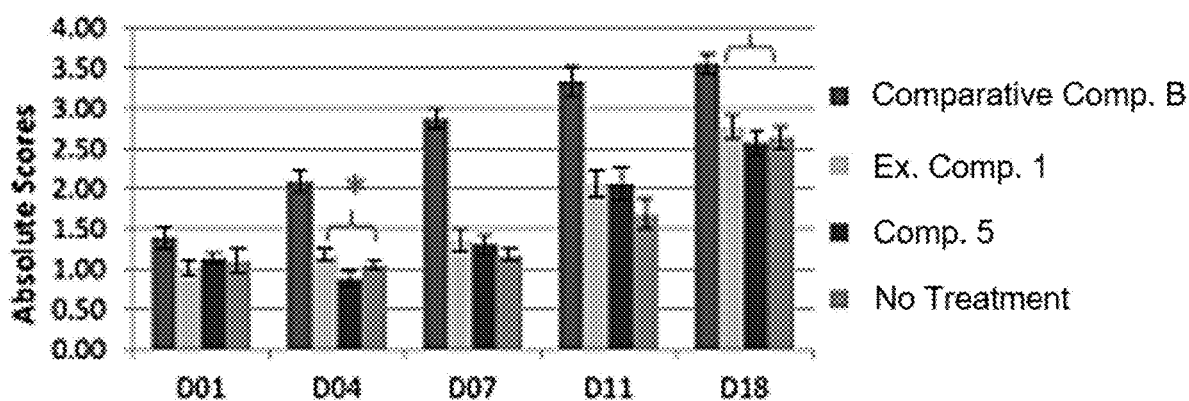
FIG. 15 is a bar graph illustrating absolute scores after receiving an application of a non-limiting exemplary skin treatment composition or a comparative composition according to aspects of the disclosure.

The extent of the wound was evaluated on a scale of 1 to 5, with 5 indicating the most healing of the wound. FIGS. 14 and 15 provide bar graphs for the epithelial confluence and general wound appearance at day 1, day 4, day 7, day 11, and day 18 after the laser treatment. The benefits of applying Composition 5 after a laser procedure are evident in FIGS. 14 and 15. Additionally, the application of the Composition 5 have accelerated level of epidethelial confluence at day 7 and day 11 as compared to placebo control. Likely, when comparing general wound appearance, the composition containing 1 wt. % of acetyl trifluoromethylphenyl valylglycine have exhibited better general wound appearance at day 4 and day 18 compared to placebo control.

Example 5

Regenerative Augmentation of Laser Procedure

Exemplary Composition 2, which contained 1 wt. % of acetyl trifluoromethylphenyl valylglycine, was evaluated in comparison to Comparative Composition B on skin that received a non-ablative fractional laser resurfacing procedure. Specifically, 33 female volunteers having skin exhibiting mild to severe crow's feet wrinkles (2-5.6/0-6 Atlas Scale); mild to severe dyschromia (3.5-8/0-9 Griffith Scale); and mild to severe roughness (3.5-8/0-9 Griffith Scale) completed this evaluation. After the volunteers received the non-ablative fractional laser resurfacing procedure, each volunteer received 5 mg of Example Composition 2 on a first half of their face and received 5 mg of Comparative Composition B on the second half of their face. The application of Example Composition 2 and Comparative Composition B occurred once in the morning and once in the afternoon or evening for 28 days. The volunteers were evaluated to assess erythema, edema, peeling, wrinkles, dyschromia, skin tone evenness, skin radiance, and skin roughness.

Figure 6:
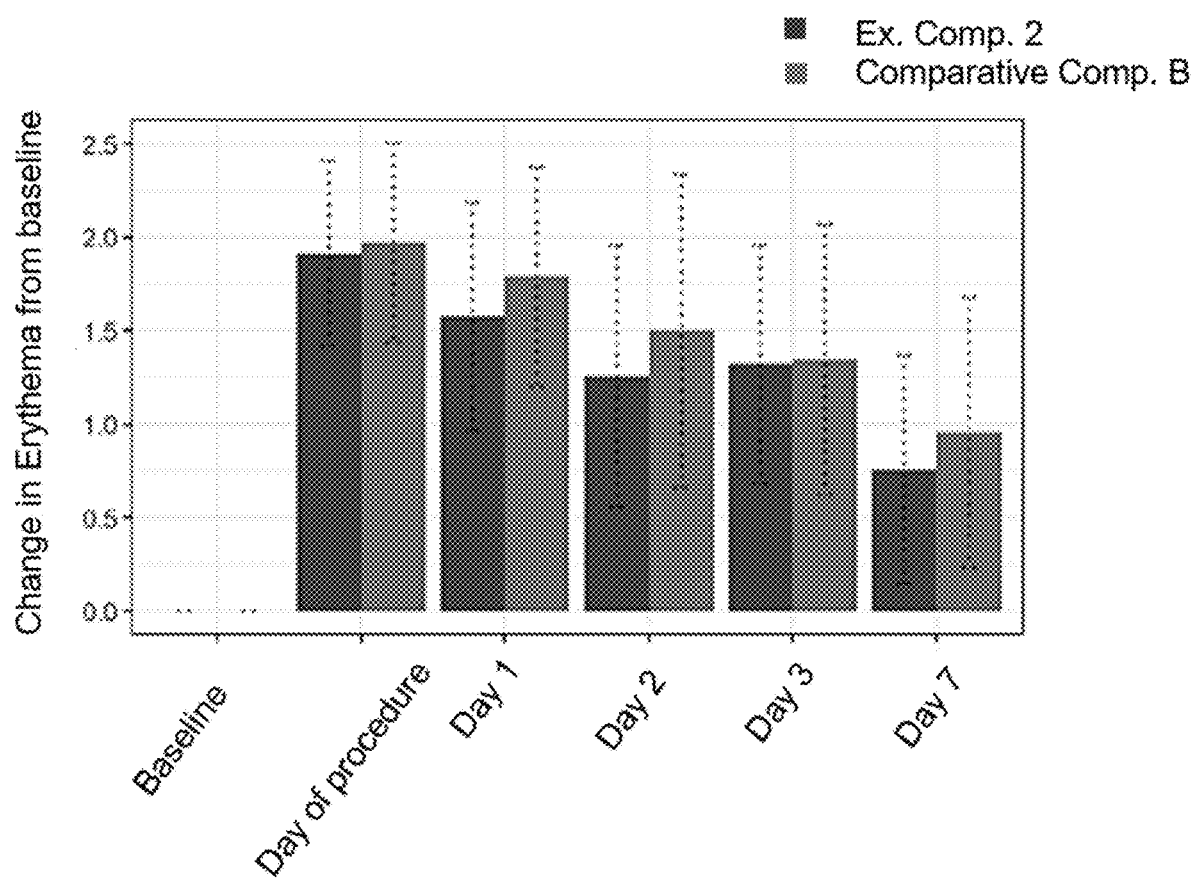
FIG. 6 is a bar graph of the change in erythema after the application of a non-limiting exemplary skin treatment composition or a comparative composition according to aspects of the disclosure.
Figure 7:
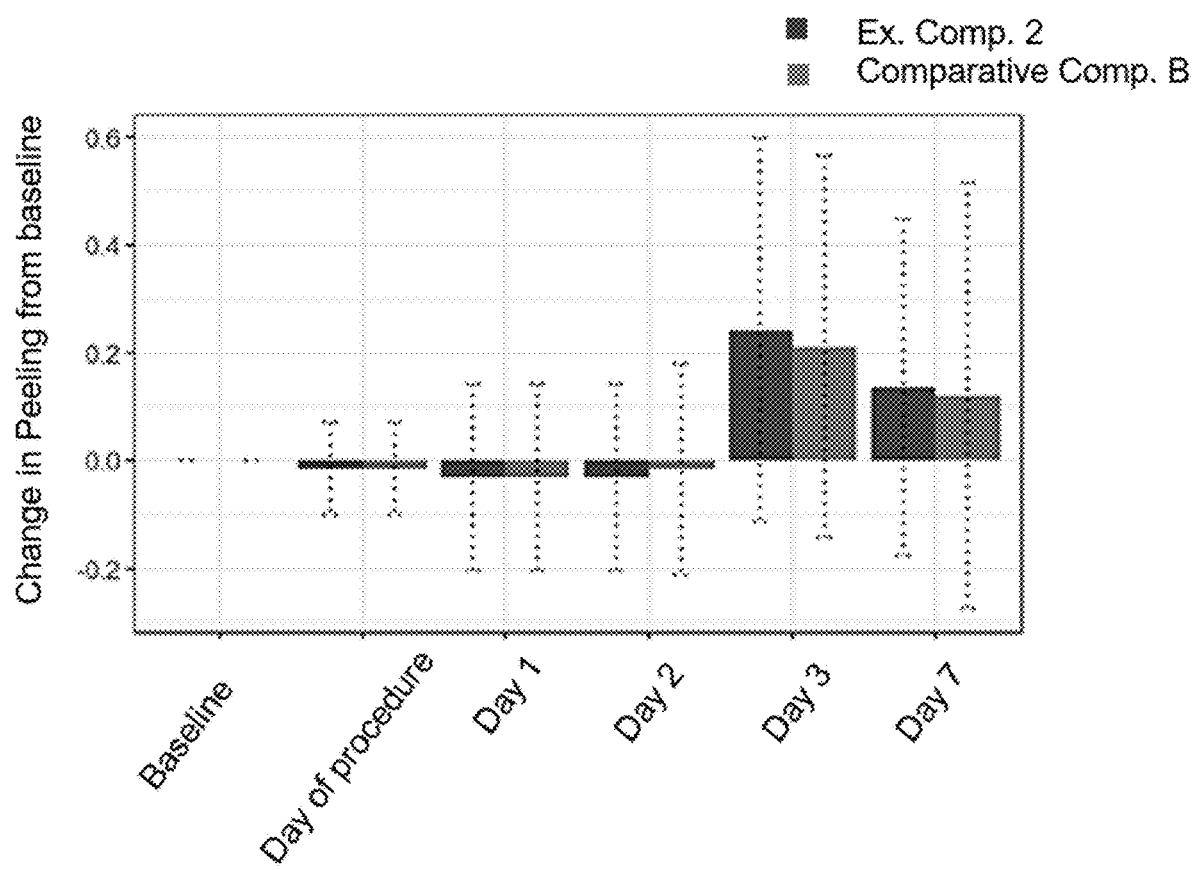
FIG. 7 is a bar graph comparing the level of peeling after receiving an application of a non-limiting exemplary skin treatment composition or a comparative composition in accordance with aspects of the disclosure.
Figure 8:
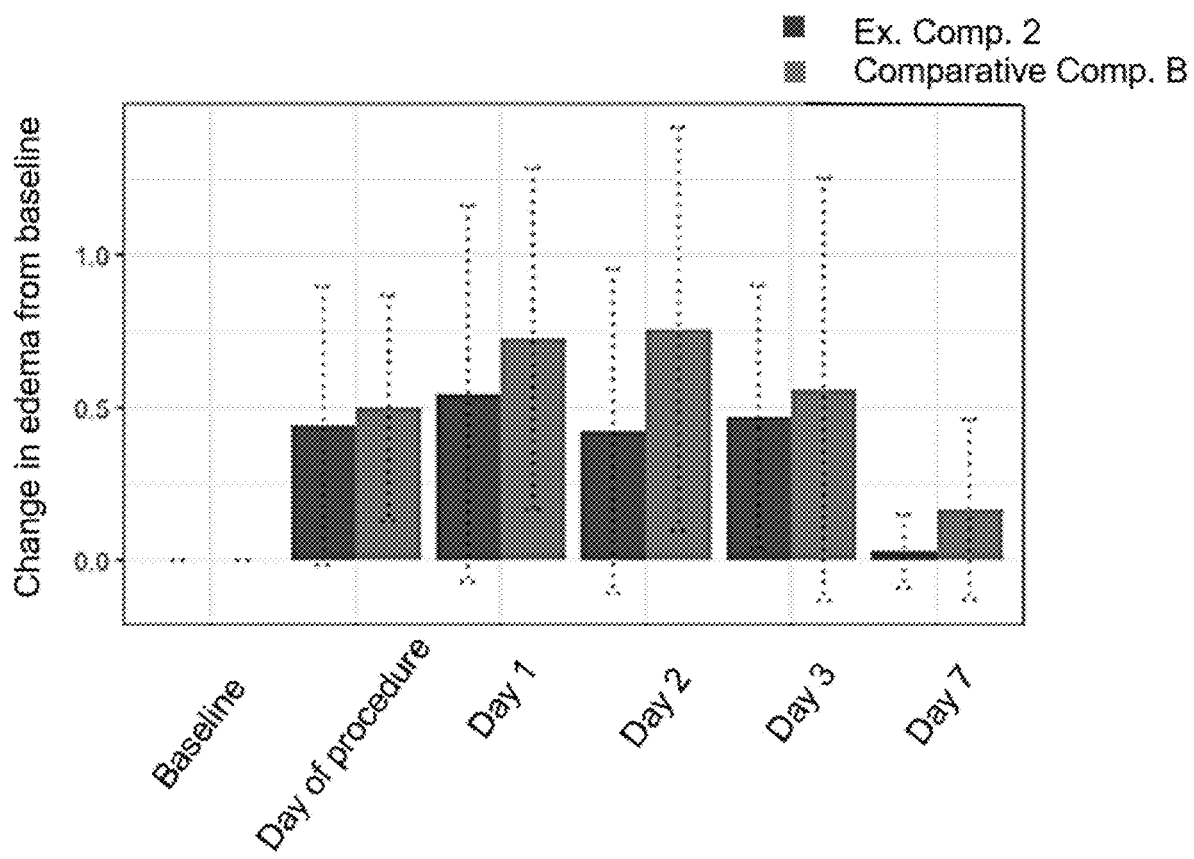
FIG. 8 is a bar graph comparing the amount of edema after receiving an application of a non-limiting exemplary skin treatment composition or a comparative composition according to aspects of the disclosure.
Figure 9:
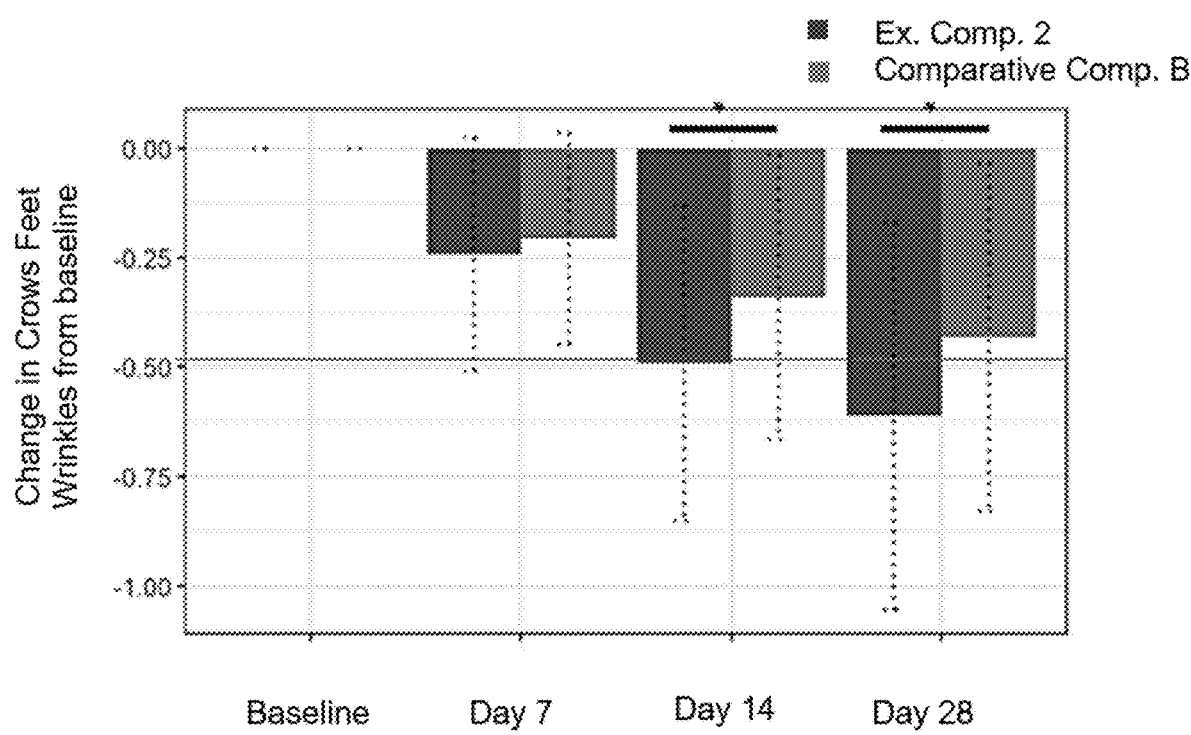
FIG. 9 is a bar graph evaluating the reduction of crow's feet wrinkles after receiving an application of a non-limiting exemplary skin treatment composition or a comparative composition according to aspects of the disclosure.
Figure 10:
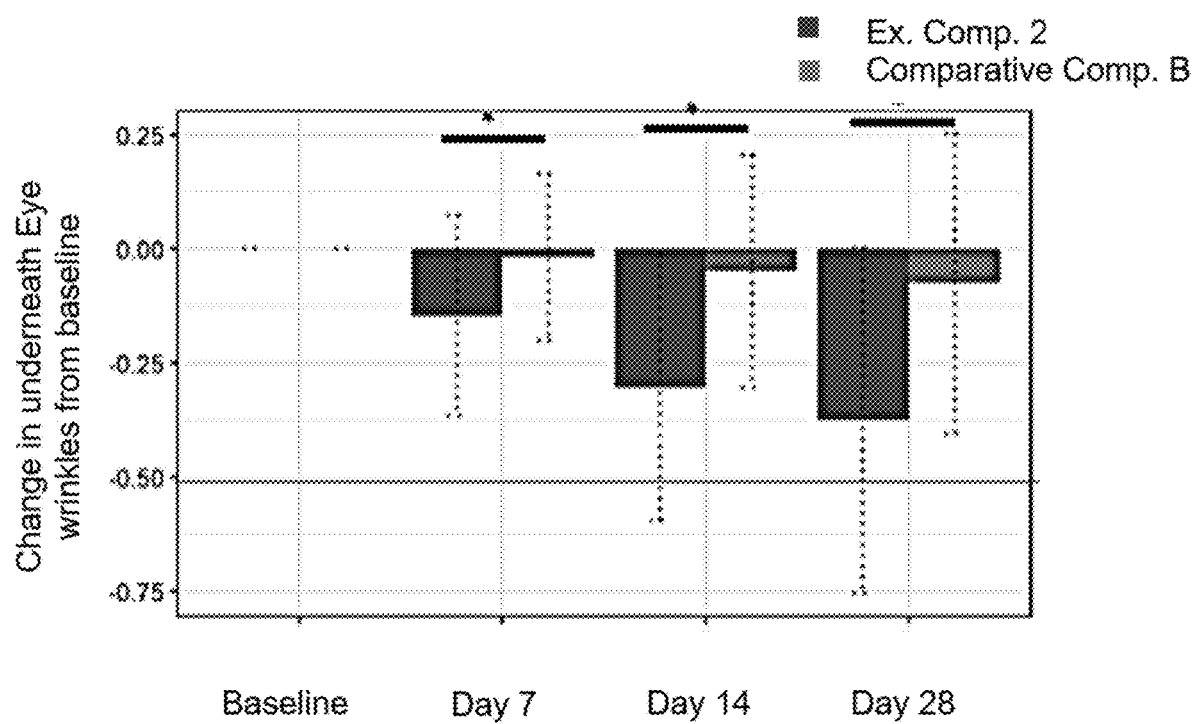
FIG. 10 is a bar graph evaluating the reduction of underneath the eye wrinkles after receiving an application of a non-limiting exemplary skin treatment composition or a comparative composition according to aspects of the disclosure.
Figure 11:
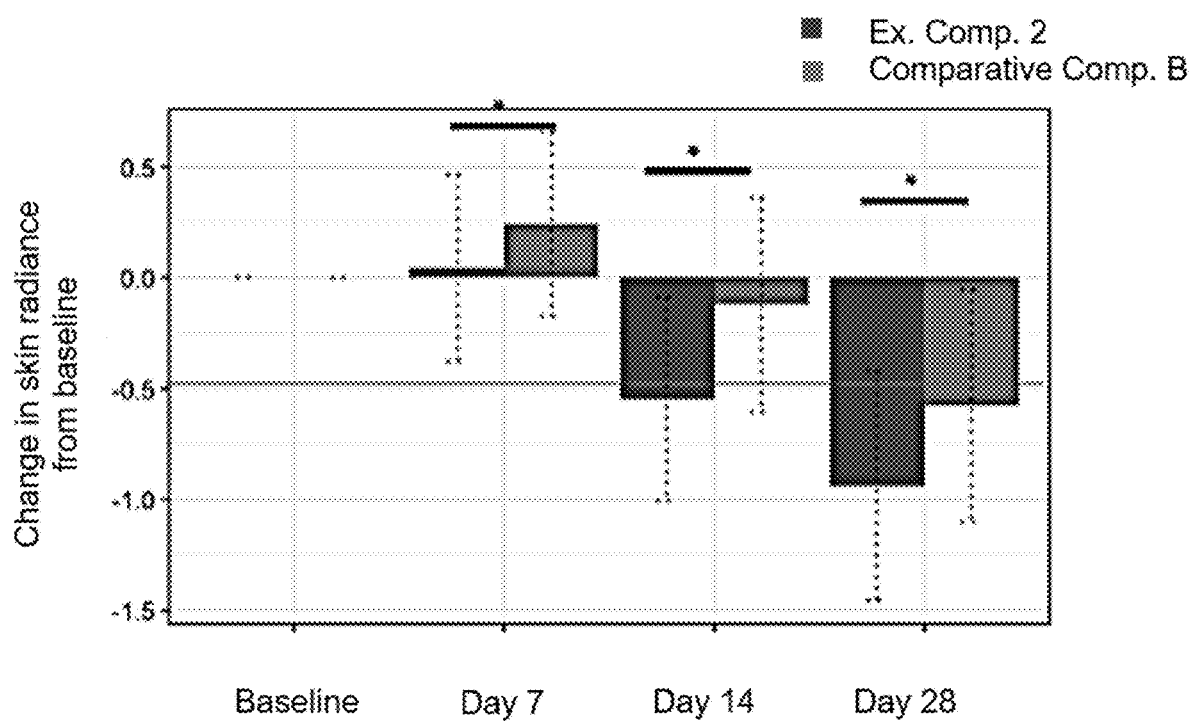
FIG. 11 is a bar graph evaluating skin radiance after receiving an application of a non-limiting exemplary skin treatment composition or a comparative composition according to aspects of the disclosure.
Figure 12:
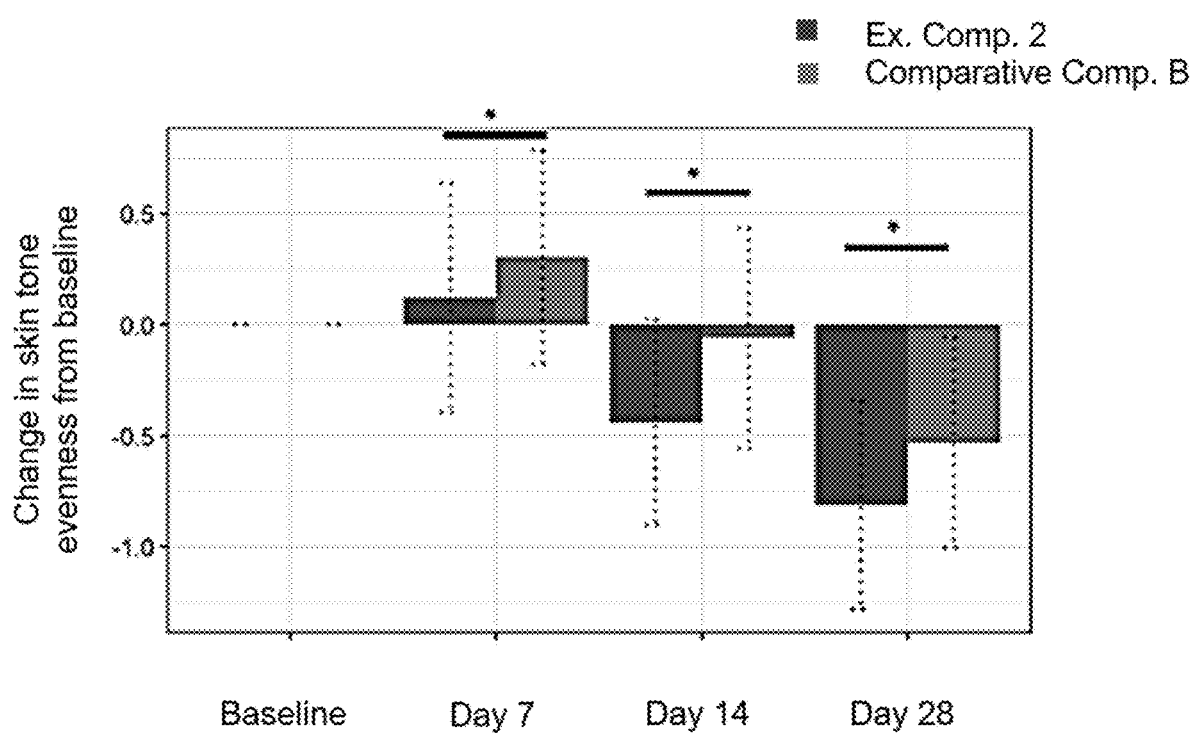
FIG. 12 is a bar graph evaluating skin tone evenness after receiving an application of a non-limiting exemplary skin treatment composition or a comparative composition according to aspects of the disclosure.
Figure 13:
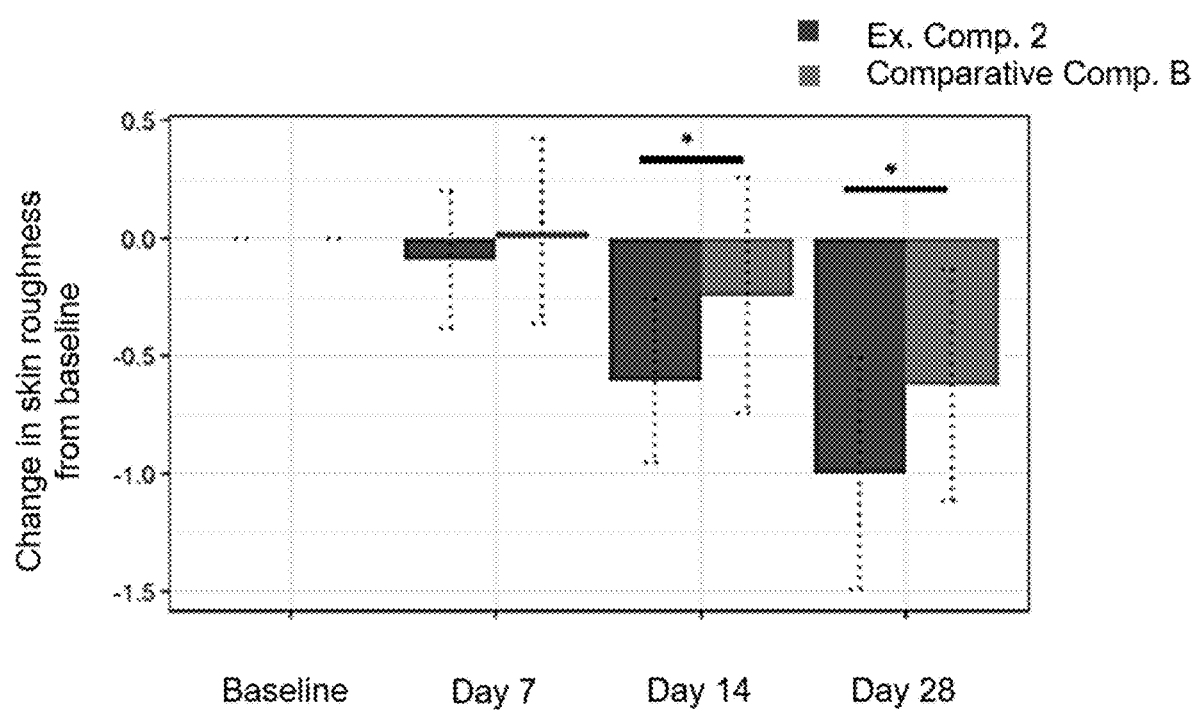
FIG. 13 is a bar graph evaluating skin roughness after receiving an application of a non-limiting exemplary skin treatment composition or a comparative composition according to aspects of the disclosure.

Example Composition 2 resulted in significant improvement to crow's feet wrinkles, under eye wrinkles, skin dyschromia, tone, evenness, and roughness. The results for the change in erythema, peeling, Edema, are presented as bar graphs in FIGS. 6-8. As seen from FIGS. 6-8, Example Composition 2 provided healing benefits that were similar to Comparative Composition B.

For anti-aging efficacy, the reduction of crow's feet wrinkles, underneath the eye wrinkles, skin radiance, skin tone evenness, and skin roughness were evaluated. Example Composition 2 exhibited superior anti-ageing efficacy when compared to Comparative Composition B. For instance, Example Composition 2 produced better reductions of crow's feet wrinkles than Comparative Composition B on day 14 and day 28. Example Composition 2 provided a significantly superior reduction in underneath the eye wrinkles as compared to Comparative Composition B on each day evaluated after application of such skin treatment compositions. Regarding skin radiance, Example Composition 2 minimized the reduction of skin radiance associated with the laser resurfacing procedure on day 7 and lead to enhanced skin radiance on days 14 and 28 when compared to Comparative Composition B. Example Composition 2 also minimized the reduction of skin tone evenness associated with the laser resurfacing procedure on day 7 and provided superior improvements to skin tone evenness on days 14 and 28 compared to Comparative Composition B. Additionally, Example Composition 2 provided significantly superior reduction in skin roughness on days 7, 14, and 28 as compared to Comparative Composition B. Bar graphs of the evaluation of the reduction of crow's feet wrinkles, underneath the eye wrinkles, skin radiance, skin tone evenness, and skin roughness are shown in FIGS. 9-13.

The invention claimed is:

1. A method for improving skin tone evenness, reducing skin roughness, or a combination thereof, the method comprising:
   (a) wounding skin by applying a laser procedure, a microneedle procedure, a cryotherapy procedure, a radiofrequency microneedle procedure, or a combination thereof, to the skin; and
   (b) applying a skin treatment composition to the wounded skin within 24 hours, the skin treatment composition comprising:
      (i) about 0.1 to about 10 wt. % of acetyl trifluoromethylphenyl valylglycine; and
      (ii) about 0.1 to about 30 wt. % of a silicone, fatty compound, or a mixture thereof; and
      (iii) water,
         wherein the skin treatment composition is an emulsion, and all weight percentages are based on a total weight of the skin treatment composition; and
   (c) accelerating wound closure and enhancing regeneration of epidermis;
      wherein the method improves skin tone evenness, reduces skin roughness, or a combination thereof, and the improvement in skin tone evenness, the reduction in skin roughness, or the combination thereof is greater compared to an improvement in skin tone evenness, a reduction in skin roughness, or a combination thereof without application of the skin treatment composition.

2. The method of claim 1, wherein the skin treatment composition comprises about 1 to about 30 wt. % of a fatty compound chosen from a fatty alcohol, a fatty ester, a fatty ether, a fatty acid, a hydrocarbon oil, or mixtures thereof.

3. The method of claim 2, wherein the skin treatment composition comprises a fatty alcohol chosen from decyl alcohol, undecyl alcohol, dodecyl alcohol, myristyl alcohol, lauryl alcohol, cetyl alcohol, stearyl alcohol, cetearyl alcohol, isostearyl alcohol, isocetyl alcohol, behenyl alcohol, linalool, oleyl alcohol, cis-4-t-butylcyclohexanol, isotridecyl alcohol, myricyl alcohol, arachidyl alcohol, or mixtures thereof.

4. The method of claim 2, wherein the skin treatment composition comprises a hydrocarbon oil that is a plant based hydrocarbon oil chosen from coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, castor oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, or mixtures thereof.

5. The method of claim 1, wherein the skin treatment composition comprises about 1 to about 30 wt. % of a silicone chosen from lauryl peg-9 polydimethylsiloxyethyl dimethicone, dimethylsiloxane, poly dimethylsiloxane, polydimethylsiloxane, dimethicone, acrylate/dimethicone polymer, or mixtures thereof.

6. The method of claim 1, wherein the skin treatment composition further comprises:
 (iv) about 0.5 to about 30 wt. % of a polyol chosen from ethylene glycol, propylene glycol, butylene glycol, hexylene glycol, pentylene glycol, diethylene glycol, dipropylene glycol, 1,3 propanediol, glycerin, polyethylene glycols, or a mixture thereof.

7. The method of claim 1, wherein the skin treatment is formulated to be a cream, a lotion, a serum, or an ampoule.

8. The method of claim 1 wherein the skin treatment composition is applied at least once per day for at least 14 days after wounding the skin.

9. The method of claim 1, wherein the skin treatment composition is applied at least twice per day for at least 14 days after wounding the skin.

10. A method for improving skin tone evenness comprising:
 (a) wounding skin by applying a laser procedure, a microneedle procedure, a cryotherapy procedure, a radiofrequency microneedle procedure, or a combination thereof, to the skin; and
 (b) applying a skin treatment composition to the wounded skin within 24 hours and applying the skin treatment composition at least once per day for at least 14 days, the skin treatment composition comprising:
  (i) about 0.1 to about 10 wt. % of acetyl trifluoromethylphenyl valylglycine;
  (ii) about 0.1 to about 30 wt. % of a silicone, fatty compound, or a mixture thereof; and
  (ii) about 40 to about 90 wt. % water;
  (iv) about 1 to about 25 wt. % of a polyol chosen from ethylene glycol, propylene glycol, butylene glycol, hexylene glycol, pentylene glycol, diethylene glycol, dipropylene glycol, 1,3 propanediol, glycerin, polyethylene glycols, or a mixture thereof;
   wherein the skin treatment composition is an emulsion, and all weight percentages are based on a total weight of the skin treatment composition; and
 (c) accelerating wound closure and enhancing regeneration of epidermis;
  wherein the method improves skin tone evenness and the improvement in skin tone evenness after 14 days is greater compared to an improvement in skin tone evenness without application of the skin treatment composition.

11. The method of claim 10, wherein the skin comprises skin around the eyes and the method reduces crow's feet wrinkles and the reduction of the crow's feet wrinkles after 14 days is greater than a reduction in the crow's feet wrinkles without application of the skin treatment composition after 14 days.

12. The method of claim 10, wherein the skin comprises skin around the eyes and the method reduces undereye wrinkles and the reduction of the undereye wrinkles after 14 days is greater than a reduction in the undereye wrinkles without application of the skin treatment composition after 14 days.

13. The method of claim 10, wherein the method reduces skin roughness and the reduction of the skin roughness after 14 days is greater than a reduction in the skin roughness without application of the skin treatment composition after 14 days.

14. The method of claim 10, wherein the skin comprises skin around the eyes and the method reduces crow's feet wrinkles, undereye wrinkles, and skin roughness and the reduction in the crow's feet wrinkles, the undereye wrinkles, and the skin roughness is greater than a reduction in the crow's feet wrinkles, the undereye wrinkles, and the skin roughness without application of the skin treatment composition after 14 days.

15. The method of claim 10, wherein the skin treatment composition comprises:
 (i) about 0.1 to about 4 wt. % of acetyl trifluoromethylphenyl valylglycine;
 (ii) about 15 to about 25 wt. % of a silicone, fatty compound, or a mixture thereof; and
 (iii) about 40 to about 90 wt. % water;
 (iv) about 5 to about 20 wt. % of a polyol chosen from ethylene glycol, propylene glycol, butylene glycol, hexylene glycol, pentylene glycol, diethylene glycol, dipropylene glycol, 1,3 propanediol, glycerin, polyethylene glycols, or a mixture thereof.

16. The method of claim 14, wherein the skin treatment composition comprises:
 (i) about 0.1 to about 4 wt. % of acetyl trifluoromethylphenyl valylglycine;
 (ii) about 15 to about 25 wt. % of a silicone, fatty compound, or a mixture thereof; and
 (iii) about 40 to about 90 wt. % water;
 (iv) about 5 to about 20 wt. % of a polyol chosen from ethylene glycol, propylene glycol, butylene glycol, hexylene glycol, pentylene glycol, diethylene glycol, dipropylene glycol, 1,3 propanediol, glycerin, polyethylene glycols, or a mixture thereof.

17. The method of claim 1, wherein the skin treatment composition is not applied to the skin as a gel.

18. The method of claim 17, wherein the skin treatment composition is free from celluloses.

19. The method of claim 15, wherein the skin treatment composition is not applied to the skin as a gel.

20. The method of claim 19, wherein the skin treatment composition is free from celluloses.

* * * * *